United States Patent
Deangelis

(10) Patent No.: US 7,972,787 B2
(45) Date of Patent: Jul. 5, 2011

(54) METHODS FOR DETECTING AGE-RELATED MACULAR DEGENERATION

(75) Inventor: Margaret M. Deangelis, Cambridge, MA (US)

(73) Assignee: Massachusetts Eye and Ear Infirmary, Boston, MA (US)

(*) Notice: Subject to any disclaimer, the term of this patent is extended or adjusted under 35 U.S.C. 154(b) by 391 days.

(21) Appl. No.: 12/032,154

(22) Filed: Feb. 15, 2008

(65) Prior Publication Data

US 2008/0206263 A1 Aug. 28, 2008

Related U.S. Application Data

(60) Provisional application No. 60/890,339, filed on Feb. 16, 2007, provisional application No. 60/970,828, filed on Sep. 7, 2007.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ........ 435/6; 435/91.2; 536/23.5; 536/24.31

(58) Field of Classification Search .................. None
See application file for complete search history.

(56) References Cited

U.S. PATENT DOCUMENTS

| | | | |
|---|---|---|---|
| 5,756,541 A | 5/1998 | Strong et al. | |
| 5,798,349 A | 8/1998 | Levy et al. | |
| 5,910,510 A | 6/1999 | Strong et al. | |
| 6,225,303 B1 | 5/2001 | Miller et al. | |
| 6,417,342 B1 | 7/2002 | Stone et al. | |
| 6,569,630 B1 | 5/2003 | Vivekananda et al. | |
| 6,593,104 B1 | 7/2003 | Stone et al. | |
| 6,869,591 B2 | 3/2005 | Lanza et al. | |
| 7,695,909 B2 | 4/2010 | Gorin et al. | |
| 2002/0102581 A1 | 8/2002 | Hageman et al. | |
| 2003/0017501 A1 | 1/2003 | Hageman et al. | |
| 2003/0138798 A1 | 7/2003 | Stone et al. | |
| 2003/0185760 A1 | 10/2003 | Lanza et al. | |
| 2003/0215392 A1 | 11/2003 | Lanza et al. | |
| 2004/0023266 A1 | 2/2004 | Vivekananda et al. | |
| 2004/0265924 A1 | 12/2004 | Hollyfield et al. | |
| 2005/0059010 A1 | 3/2005 | Stone et al. | |
| 2005/0130167 A1 | 6/2005 | Bao et al. | |
| 2005/0272049 A1 | 12/2005 | Banerjee et al. | |
| 2006/0127915 A1* | 6/2006 | Klein et al. ........ | 435/6 |
| 2006/0263897 A1 | 11/2006 | Stapert et al. | |
| 2006/0281120 A1 | 12/2006 | Gorin et al. | |
| 2007/0020701 A1 | 1/2007 | Menon et al. | |
| 2008/0255000 A1 | 10/2008 | Dogulu et al. | |
| 2009/0017029 A1 | 1/2009 | Hoh et al. | |

FOREIGN PATENT DOCUMENTS

| | | |
|---|---|---|
| WO | WO-0106262 | 1/2001 |
| WO | WO-0184149 | 11/2001 |
| WO | WO-2006062716 A2 | 6/2006 |
| WO | WO-2006088950 | 8/2006 |
| WO | WO-2006133295 A2 | 12/2006 |
| WO | WO-2007044897 A1 | 4/2007 |
| WO | WO-2008013893 A2 | 1/2008 |
| WO | WO-2008067551 A2 | 6/2008 |
| WO | WO-2008094370 A2 | 8/2008 |
| WO | WO-2008103299 A2 | 8/2008 |
| WO | WO-2008110828 A1 | 9/2008 |
| WO | WO-2008103299 A3 | 12/2008 |

OTHER PUBLICATIONS

Hirschhorn et al. Genetics in Medicine. Mar. 2002. vol. 4, No. 2, pp. 45-61.*
Yang et all. Science. 2006. 314: 992-993 and supplemental online content.*
GeneCard for the HTRA1 gene available via url: <genecards.org/cgi-bin/carddisp.pl?gene=Htra1>, printed Jul. 20, 2010.*
Lucentini et al. The Scientist (2004) vol. 18, p. 20.*
Wacholder et al. J. Natl. Cancer Institute (2004) 96(6):434-442.*
Ioannidis et al. Nature genetics (2001) 29:306-309.*
Halushka et al. Nature. Jul. 1999. 22: 239-247.*
"HtrA1 : A novel TGFβ antagonist," Development (2003) 131:502.
Adams et al. "HTRA1 Genotypes Associated with Risk of Neovascular Age-related Macular Degeneration Independent of CFH and Smoking." ARVO Abstract, Control/Tracking No. 07-A-2553-ARVO. Abstract available Feb. 16, 2007.
Adams et al. "Analysis of the HTRA1 Gene in Patients with Neovascular Age-related Macular Degeneration," ARVO Poster No. B495, Program No. 4623. May 6, 2007.
Age-Related Eye Disease Study Research Group (2001) "The Age-Related Eye Disease Study system for classifying age-related macular degeneration from stereoscopic color fundus photographs: the Age-Related Eye Disease Study Report No. 6," Am J Ophthalmol. 132(5):668-81.
Age-Related Eye Disease Study Research Group (2005) "The Age-Related Eye Disease Study severity scale for age-related macular degeneration: AREDS Report No. 17," Arch Ophthalmol. 123(11):1484-98.
Age-Related Eye Disease Study Research Group (2005) "Risk Factors for the Incidence of Advanced Age-Related Macular Degeneration in the Age-Related Eye Disease Study (AREDS): AREDS report No. 19," Ophthalmology 112(4):533-539.
Baldi et al. (2002) "The HtrA1 serine protease is down-regulated during human melanoma progression and represses growth of metastatic melanoma cells," Oncogene 21:6684-6688.
Cameron et al. (2007) "HTRA1 variant confers similar risks to geographic atrophy and neovascular age-related macular degeneration," Cell Cycle 6(9):1122-5.
Chen et al. (2007) "Retinopathy of prematurity," Angiogenesis 10(2):133-40.

(Continued)

*Primary Examiner* — Carla Myers
(74) *Attorney, Agent, or Firm* — Goodwin Procter LLP

(57) ABSTRACT

The invention provides methods and compositions for determining whether a subject is at risk of developing age-related macular degeneration, for example, the wet or neovascular form of age-related macular degeneration. The method involves determining whether the subject has a protective variant and/or a risk variant at a polymorphic site in the HTRA1 gene. In addition, the invention provides a method of treating or slowing the progression of age-related macular degeneration by reducing the expression of the HTRA1 gene, or reducing the biological activity of the HTRA1 gene product.

11 Claims, 13 Drawing Sheets

OTHER PUBLICATIONS

Chen et al. (2008) "Meta-analysis of the Association of the HTRA1 Polymorphisms with the risk of Age-related Macular Degeneration," Experimental Eye Research, Article in Press, doi:10.1016/j.exer.2008.10.017, 23 pages.

Chien et al. (2006) "Serine protease HtrA1 modulates chemotherapy-induced cytotoxicity." J Clin Invest. 116(7):1994-2004.

Chien, J. et al. (2004) "A candidate tumor suppressor HtrA1 is downregulated in ovarian cancer," Oncogene 23:1636-1644.

Churchill et al. (2007) "A potential therapeutic target in age-related macular degeneration," Therapy 4(2):167-170.

Cibelli, G. et al. (2002) "Nitric Oxide-Induced Programmed Cell Death in Human Neuroblastoma Cells is Accompanied by the Synthesis of Egr-1, a Zinc Finger Transcription Factor," Journal of Neuroscience Research 67:450-460.

Clausen et al. (2002) "The HtrA family of proteases: implications for protein composition and cell fate," Mol Cell. 10(3):443-55.

Conley et al. (2006) "CFH, ELOVL4, PLEKHA1 and LOC387715 genes and susceptibility to age-related maculopathy: AREDS and CHS cohorts and meta-analyses," Hum Mol Genet. 5(21):3206-18.

Database dbsnp, NCBI, accessed Apr. 21, 2009, http://www.ncbi.nlm.nih.gov/snp/snp_ref.cgl?RS=10490924, Database accession No. rs10490924.

Database dbsnp, NCBI, accessed Apr. 21, 2009, http://www.ncbi.nlm.nih.gov/snp/snp_ref.cgl?RS=1049331, Database accession No. rs1049331.

Database dbsnp, NCBI, accessed Apr. 21, 2009, http://www.ncbi.nlm.nih.gov/snp/snp_ref.cgl?RS=10664316, Database accession No. rs10664316.

Database dbsnp, NCBI, May 25, 2006, http://www.ncbi.nlm.nih.gov/snp/snp_ref.cgl?RS=11200638, Database accession No. rs11200638.

Database dbsnp, NCBI, accessed Apr. 21, 2009, http://www.ncbi.nlm.nih.gov/snp/snp_ref.cgl?RS=11200638, Database accession No. rs11200638.

Database dbsnp, NCBI, May 4, 2006, http://www.ncbi.nlm.nih.gov/snp/snp_ref.cgl?RS=2293870, Database accession No. rs2293870.

Database dbsnp, NCBI, accessed Aug. 2, 2007, http://www.ncbi.nlm.nih.gov/snp/snp_ref.cgl?RS=2293870, Database accession No. rs2293870.

Database dbsnp, NCBI, accessed Apr. 21, 2009, http://www.ncbi.nlm.nih.gov/snp/snp_ref.cgl?RS=2293870, Database accession No. rs2293870.

Database dbsnp, NCBI, May 25, 2006, http://www.ncbi.nlm.nih.gov/snp/snp_ref.cgl?RS=2672598, Database accession No. rs2672598.

Database dbsnp, NCBI, accessed Apr. 21, 2009, http://www.ncbi.nlm.nih.gov/snp/snp_ref.cgl?RS=2672598, Database accession No. rs2672598.

DeAngelis et al. (2004) "Extremely Discordant Sib-Pair Study Design to Determine Risk Factors for Neovascular Age-Related Macular Degeneration," Arch Ophthalmol. 122(4):575-80.

DeAngelis et al. (2007) "Alleles in the HtrA Serine Peptidase 1 Gene Alter the Risk of Neovascular Age-Related Macular Degeneration." Ophthalmology, 115:1209-1215E7.

DeAngelis et al. (2007) "Cigarette smoking, CFH, APOE, ELOVL4, and risk of neovascular age-related macular degeneration." Arch Ophthalmol. 125(1):49-54.

DeAngelis, Margaret "Sibling Study of Age-Related Macular Degeneration," Computer Retrieval of Information on Scientific Projects, Abstract for Grant No. 5R01EY014458-05, Fiscal Year 2007.

DeLuca et al. (2003) "Distribution of the Serine Protease HtrA1 in Normal Human Tissues," The Journal of Histochemistry & Cytochemistry 51(10):1279-1284.

DeLuca et al. (2004) "The Serine Protease HtrA1 Is Upregulated in the Human Placenta During Pregnancy," Journal of Histochemistry & Cytochemistry 52(7):885-892.

DeWan et al. (2006) "HTRA1 promoter polymorphism in wet age-related macular degeneration," Sciencexpress, Sciencexpress.Org, 10.1126/Science.1133807, p. 1-7.

DeWan et al. (2006) "HTRA1 promoter polymorphism in wet age-related macular degeneration," Science Supporting Online Information, http://www.sciencemag.org/cgi/data/1133807/DC1, p. 1-13 and Figures S1-S7.

Edwards et al. (2005) "Complement factor H polymorphism and age-related macular degeneration," Science 308(5720):421-4.

Fine et al. (2000) "Age-related macular degeneration," N. Engl J Med. 342(7):483-92.

Fisher et al. (2005) "Meta-analysis of genome scans of age-related macular degeneration," Hum Mol Genet 14(15):2257-64.

Gabriel et al. (2002) "The structure of haplotype blocks in the human genome," Science 296(5576):2225-9.

Gerstein et al. (2007) "What is a gene, post-ENCODE? History and updated definition," Genome Res 17(6):669-81.

Gibbs et al. (2008) "Further Mapping of 10q26 supports strong association of HTRA1 polymorphisms with age-related macular degeneration," Vision Research 48:685-689.

Gold et al. (2006) "Variation in factor B (BF) and complement component 2 (C2) genes is associated with age-related macular degeneration," Nat Genet., Advance online Publication, doi:10:1038/ng1750, p. 1-5.

Grau et al. (2005) "Implications of the serine protease HtrA1 in amyloid precursor processing," Proceedings of the National Academy of Sciences 102(17):6021-26.

Grau et al. (2006) "The Role of Human HtrA1 in Arthritic Disease," The Journal of Biological Chemistry 281(10):6124-6129.

Greally (2007) "Encyclopaedia of humble DNA." Nature 447(7146):782-3.

Grevin et al. (1996) "Structure and organization of the mouse *elk1* gene," Gene 174:185-188.

Haddad et al. (2006) "The Genetics of Age-Related Macular Degeneration: A Review of Progress to Date," Survey of Ophthalmology 51(4):316-363.

Hageman et al. (2005) "A common haplotype in the complement regulatory gene factor H (HF1/CFH) predisposes individuals to age-related macular degeneration," Proc Natl Acad Sci U S A. 102(20):7227-32.

Haines et al. (2005) "Complement factor H variant increases the risk of age-related macular degeneration." Science 308(5720):419-21.

Hawkins et al. (1999) "Epidemiology of age-related macular degeneration," Mol. Vis. 5:26.

Hu et al. (1998) "Human HtrA, an Evolutionarily Conserved Serine Protease Identified as a Differentially Expressed Gene Product in Osteoarthritic Cartilage," The Journal of Biological Chemistry 273(51):34406-34412.

International Search Report for Application No. PCT/US2008/002061, dated Sep. 17, 2008, 9 pages.

Invitation to Pay Additional Fees and, Where Applicable, Protest Fee and Annex thereto, for Application No. PCT/US2008/002061, dated Jul. 10, 2008, 9 pages.

Jakobsdottir et al. (2005) "Susceptibility genes for age-related maculopathy on chromosome 10q26," Am J Hum Genet. 77(3):389-407.

Kang-Park et al. (2003) "PTEN modulates insulin-like growth factor II (IGF-II)-mediated signaling; the protein phosphatase activity of PTEN downregulates IGF-II expression in hepatoma cells." FEBS Lett. 545(2-3):203-8.

Kim et al. (2003) "Crystal Structure of the Protease Domain of a Heat-shock Protein HtrA from *Thermotoga maritime*," The Journal of Biological Chemistry 278(8):6543-6551.

Kim et al. (2005) "Structure and Function of HtrA Family Proteins, the Key Players in Protein Quality Control," Journal of Biochemistry and Molecular Biology 38(3):266-274.

Klein et al. (2005) "Complement factor H polymorphism in age-related macular degeneration." Science 308(5720):385-9.

Knebel et al. (2005) "Reduced phosphorylation of transcription factor Elk-1 in cultured fibroblasts of a patient with premature aging syndrome and insulin resistance," Exp Clin Endocrinol Diabetes 113(2):94-101.

Kobiela et al., (2003) "Activation of mGST and the HtrA1 serine protease down regulation by oxidative stress in experimental hormonally induced cancer," European Journal of Biochemistry 1 Supplement 1: Abstract No. P3.8-17.

Marx (2006) "Gene offers insight into macular degeneration," Science. 314(5798):405.

Miller et al. (1999) "Photodynamic therapy with verteporfin for choroidal neovascularization caused by age-related macular degeneration: results of a single treatment in a phase 1 and 2 study," Arch Ophthalmol. 117(9):1161-73.

Missiakas et al. (1998) "The extracytoplasmic function sigma factors: role and regulation," Molecular Microbiology 28(6):1059-1066.

Murwantoko et al. (2004) "Binding of proteins to the PDZ domain regulates proteolytic activity of HtrA1 serine protease," Biochem. J. 381:894-904.

Oka et al. (2003) "HtrA1 serine protease inhibits signaling mediated by Tgfβ family proteins," Development 131:1041-1053.

Pedersen et al. (2001) "HtrA Homologue of *Legionella pneumophila*: an Indispensable Element for Intracellular Infection of Mammalian but Not Protozoan Cells," Infection and Immunity 69(4):2569-2579.

Risch et al. (1995) "Extreme discordant sib pairs for mapping quantitative trait loci in humans," Science 268(5217):1584-9.

Rivera et al. (2005) "Hypothetical LOC387715 is a second major susceptibility gene for age-related macular degeneration, contributing independently of complement factor H to disease risk," Hum Mol Genet. 14(21):3227-36.

Schmidt et al. (2006) "Cigarette smoking strongly modifies the association of LOC387715 and age-related macular degeneration," Am J Hum Genet. 78(5):852-64.

Sharon et al. (2003) "Shared Mutations in NR2E3 in Enhanced S-cone Syndrome, Goldmann-Favre Syndrome, and Many Cases of Clumped Pigmentary Retinal Degeneration," Ophthalmic Molecular Genetics 121:1316-1323.

Shaw et al. (2004) "Insulin Like Growth Factor-1 and Insulin-Like Growth Factor Binding Proteins: Their Possible Roles in Both Maintaining Normal Retinal Vascular Function and in Promoting Retinal Pathology," Reviews in Endocrine & Metabolic Disorders 5:199-207.

Shuler et al. (2007) "Neovascular age-related macular degeneration and its association with LOC387715 and complement factor H polymorphism." Arch Ophthalmol. 125(1):63-7.

The ENCODE Project Consortium (2007) "Identification and analysis of functional elements in 1% of the human genome by the ENCODE pilot project," Nature 447(7146):799-816.

Thornton et al. (2005) "Smoking and age-related macular degeneration: a review of association," Eye 19(9):935-44.

Vanhoutte et al. (2001) "Opposing roles of Elk-1 and its brain-specific isoform, short Elk-1, in nerve growth factor-induced PC12 differentiation," J Biol Chem 276(7):5189-96.

Written Opinion of the International Searching Authority for Application No. PCT/US2008/002061, dated Sep. 17, 2008, 15 pages.

Yang et al. (2006) "A variant of the HTRA1 gene increases susceptibility to age-related macular degeneration," ScienceExpress, www.sciencexpress.org, 10.1126/science.133811, p. 1-5.

Zareparsi et al. (2005) "Strong association of the Y402H variant in complement factor H at 1q32 with susceptibility to age-related macular degeneration," Am J Hum Genet. 77(1):149-53.

Zumbrunn et al. (1996) "Primary structure of a putative serine protease specific for IGF-binding proteins," FEBS Letters 398:187-192.

Cantsilieris et al. (2009) "Recent Patents Relating to Diagnostic Advances in Age Related Macular Degeneration (AMD)," *Recent Patents on DNA & Gene Sequences* 3:102-113.

Francis et al. (2008) "Joint effects of polymorphisms in the HTRA1, LOC387715/ARMS2, and CFH genes on AMD in a Caucasian population," *Mol Vis*. 14:1395-1400.

Seddon et al. (2003) "A Genomewide Scan for Age-Related Macular Degeneration Provides Evidence for Linkage to Several Chromosomal Regions." *Am J Hum Genet* 73:780-790.

Tam et al. (2008) "HTRA1 Variants in Exudative Age-Related Macular Degeneration and Interactions with Smoking and CFH," *Invest Opthalmol Vis Sci*. 49(6):2357-2365.

Weeks et al. (2000) "A full genome scan for age-related maculopathy " *Human Molecular Genetics* 9:1329-1349.

Weeks et al. (2004) "Age-Related Maculopathy: a Genomewide Scan with Continued Evidence of Susceptibility Loci within the 1q31, 10q26, and 17q25 Regions," *Am J Hum Genet* 75:174-189.

Yoshida et al. (2007) "HTRA1 promoter polymorphism predisposes Japanese to age-related macular degeneration," *Mol Vis*. 13:545-548.

Zhang et al. (2008) "The NEI/NCBI dbGAP database: genotypes and haplotypes that may specifically predispose to risk of neovascular age-related macular degeneration," *BMC Med Genet*.9:51, 10 pages.

\* cited by examiner

| SNP | Number of informative families | Variance (S) | Z value | PW p value | FW p value |
|---|---|---|---|---|---|
| PLEKHA1 rs1045216 | 16 | 16.000 | 0.500 | 0.6171 | 1.0 |
| LOC387715 rs10490923 | 3 | **** | **** | **** | **** |
| LOC387715 rs2736911 | 2 | **** | **** | **** | **** |
| LOC387715 rs10490924 | 31 | 31.000 | 4.131 | 0.000036 | 0.001 |
| LOC387715 rs10664316 | 47 | 47.000 | 4.230 | 0.000023 | 0.0007 |
| LOC387715 rs7088128 | 25 | 25.000 | 2.600 | 0.009322 | 0.27 |
| HTRA1 rs11200638 | 28 | 28.000 | 4.158 | 0.000032 | 0.0009 |
| HTRA1 -502 (from ATG$^a$) | 2 | **** | **** | **** | **** |
| HTRA1 rs2672598 | 27 | 27.000 | 3.657 | 0.000256 | 0.007 |
| HTRA1 rs1049331 | 29 | 29.000 | 4.271 | 0.000019 | 0.0006 |
| HTRA1 rs2293870 (T vs. G/C) | 61 | 26.500 | 4.662 | $3.13 \times 10^{-6}$ | 0.00009 |
| HTRA1 rs2293870 (G vs. T/C) | 65 | 26.000 | 5.295 | $1.19 \times 10^{-6}$ | 0.00003 |
| HTRA1 rs2239586 | 2 | **** | **** | **** | **** |
| HTRA1 rs2239587 | 2 | **** | **** | **** | **** |
| HTRA1 rs2672582 | 29 | 29.000 | 1.671 | 0.0947 | 1.0 |
| HTRA1 intron 5 (del GTTT) | 41 | 41.000 | 0.781 | 0.4349 | 1.0 |
| HTRA1 rs2672583 | 29 | 29.000 | 2.043 | 0.0411 | 1.0 |
| HTRA1 rs2672585 | 60 | 19.500 | 2.491 | 0.0127 | 0.37 |
| HTRA1 rs2272599 | 35 | 35.000 | 1.859 | 0.0630 | 1.83 |
| HTRA1 rs2293871 | 4 | 4.000 | 2.000 | 0.0455 | 1.32 |

FIG. 2

| D10S1213 | | D10S1656 | | D10S1723 | | D10S587 | | D10S1690 | | D10S1230 | | D10S1483 | | D10S1222 | |
|---|---|---|---|---|---|---|---|---|---|---|---|---|---|---|---|
| # of 0's = | 21 | # of 0's = | 51 | # of 0's = | 21 | # of 0's = | 20 | # of 0's = | 4 | # of 0's = | 10 | # of 0's = | 10 | # of 0's = | 7 |
| # of 1's = | 67 | # of 1's = | 55 | # of 1's = | 71 | # of 1's = | 60 | # of 1's = | 37 | # of 1's = | 44 | # of 1's = | 48 | # of 1's = | 59 |
| # of 2's = | 42 | # of 2's = | 24 | # of 2's = | 41 | # of 2's = | 51 | # of 2's = | 30 | # of 2's = | 32 | # of 2's = | 38 | # of 2's = | 35 |
| total = | 130 | total = | 130 | total = | 133 | total = | 131 | total = | 71 | total = | 86 | total = | 96 | total = | 101 |
| # of na = | 4 | # of na = | 4 | # of na = | 1 | # of na = | 3 | # of na = | 63 | # of na = | 48 | # of na = | 38 | # of na = | 33 |
| h = | 0.827 | h = | 0.750 | h = | 0.884 | h = | 0.793 | h = | 0.650 | h = | 0.740 | h = | 0.830 | h = | 0.730 |
| Chi-sq = | 0.480 | Chi-sq = | 73.261 | Chi-sq = | 1.403 | Chi-sq = | 0.360 | Chi-sq = | 2.902 | Chi-sq = | 0.781 | Chi-sq = | 3.429 | Chi-sq = | 7.072 |
| p value = | 0.787 | p value = | 1.23 x10$^{-16}$ | p value = | 0.496 | p value = | 0.835 | p value = | 0.234 | p value = | 0.677 | p value = | 0.180 | p value = | 0.029 |
| ṗ = | 1 | ṗ = | 9.88 x10$^{-16}$ | ṗ = | 1 | ṗ = | 1 | ṗ = | 1 | ṗ = | 1 | ṗ = | 1 | ṗ = | 0.223 |

FIG. 3

| Order | LOC387715 rs10490923 | LOC387715 rs2736911 | LOC387715 rs10490924 | LOC387715 rs10664316 | LOC387715 rs7088128 | HTRA1 rs11200638 | HTRA1 -502 (from ATG$^a$) C>T | HTRA1 rs2672598 | HTRA1 rs10493331 | Number of Informative Families | Frequency | p value* |
|---|---|---|---|---|---|---|---|---|---|---|---|---|
| h1 | G | C | G | - | A | G | C | C | C | 47 | 0.347 | 0.1113 |
| h2 | G | C | T | AT | A | A | C | C | T | 27 | 0.235 | 0.00002 |
| h3 | G | C | G | AT | A | G | C | C | C | 24 | 0.104 | 0.2304 |
| h4 | G | C | G | - | A | G | C | T | C | 16 | 0.104 | 0.1433 |
| h5 | G | C | G | AT | G | G | C | C | C | 15 | 0.078 | 0.4555 |
| h6 | G | C | G | - | G | G | C | T | C | 10 | 0.060 | 0.0010 |

FIG. 4

| Risk Factor | Referent | Odds Ratio (95% C.I.) | p value |
|---|---|---|---|
| LOC387715 rs10490924 "T" is rare allele | | | |
| rs10490924 TT | GG | 61.91 (10.89-352.01) | 0.0000033 |
| rs10490924 TG | GG | 5.32 (1.82-15.52) | 0.0022 |
| Smoking ≥ 10 pack-years | < 10 pack-years | 3.81 (1.84-7.91) | 0.0003 |
| CFH CC | TT | 18.13 (4.20-78.22) | 0.0001 |
| CFH TC | TT | 1.78 (0.72-4.40) | 0.2089 |
| LOC387715 rs10664316 "del AT" is rare allele | | | |
| rs10664316 del AT/del AT | AT/AT | 0.09 (0.02-0.36) | 0.0007 |
| rs10664316 del AT/AT | AT/AT | 0.30 (0.13-0.72) | 0.0069 |
| Smoking ≥ 10 pack-years | < 10 pack-years | 3.00 (1.58-5.70) | 0.0008 |
| CFH CC | TT | 12.64 (3.26-49.04) | 0.0002 |
| CFH TC | TT | 1.56 (0.68-3.58 ) | 0.2998 |
| HTRA1 rs11200638 "A" is rare allele | | | |
| rs11200638 AA | GG | 98.41 (13.45-720.08) | 0.0000062 |
| rs11200638 AG | GG | 6.05 (2.13-17.21) | 0.0007 |
| Smoking ≥ 10 pack-years | < 10 pack-years | 4.08 (1.93-8.63) | 0.0002 |
| CFH CC | TT | 19.59 (4.36-88.03) | 0.0001 |
| CFH TC | TT | 1.69 (0.67-4.26) | 0.2687 |
| HTRA1 rs2672598 "T" is rare allele | | | |
| rs2672598 TT | CC | 0.03 (0.01-0.14) | 0.000013 |
| rs2672598 TC | CC | 0.12 (0.04-0.39) | 0.0004 |
| Smoking ≥ 10 pack-years | < 10 pack-years | 3.48 (1.73-7.01) | 0.0005 |
| CFH CC | TT | 10.34 (2.76-38.67) | 0.0005 |
| CFH TC | TT | 1.69 (0.70-4.06) | 0.2428 |
| HTRA1 rs1049331 "T" is rare allele | | | |
| rs1049331 TT | CC | 105.52 (14.64-760.50) | 0.0000038 |
| rs1049331 TC | CC | 5.97 (2.10-16.99) | 0.0008 |
| Smoking ≥ 10 pack-years | < 10 pack-years | 4.09 (1.93-8.66) | 0.0002 |
| CFH CC | TT | 19.29 (4.28-86.94) | 0.0001 |
| CFH TC | TT | 1.67 (0.66-4.20) | 0.2754 |
| HTRA1 rs2293870 "T" and "C" are rare alleles | | | |
| rs2293870 CC, CT or TT | GG | 25.97 (6.32-106.66) | 0.0000062 |
| rs2293870 CG or TG | GG | 5.89 (1.96-17.71) | 0.0016 |
| Smoking ≥ 10 pack-years | < 10 pack-years | 3.31 (1.66-6.60) | 0.0006 |
| CFH CC | TT | 13.94 (3.37-57.67) | 0.0003 |
| CFH TC | TT | 1.58 (0.64 -3.90) | 0.3227 |

FIG. 5

| Exposure | Relative Risk | Frequency in cases, θ | Adjusted PAR (95% Confidence Interval) |
|---|---|---|---|
| LOC387715 rs10490924 | | | |
| TT vs. GG | 61.9 | 0.34 | 0.33 (0.25-0.41) |
| TG vs. GG | 5.3 | 0.39 | 0.32 (0.25-0.38) |
| Smoking | | | |
| (<10 pack-years vs. ≥10 pack-years) | 3.8 | 0.54 | 0.40 (0.34-0.46) |
| Smoking ≥10 pack-years or T allele[a] | 4.0 | 0.87 | 0.65 (0.61-0.69) |
| CFH CC vs. TT | 18.1 | 0.34 | 0.32 (0.24-0.39) |
| Smoking ≥10 pack-years or T allele or CFH CC[a] | 10.3 | 0.90 | 0.81 (0.77-0.86) |
| | | | |
| LOC387715 rs10664316 | | | |
| AT/AT vs del AT/del AT | 11.5 | 0.57 | 0.52 (0.44-0.60) |
| AT/AT vs. del AT/AT | 3.5 | 0.31 | 0.22 (0.16-0.28) |
| Smoking | | | |
| (<10 pack-years vs. ≥10 pack-years) | 3.0 | 0.54 | 0.36 (0.31-0.42) |
| Smoking ≥10 pack-years or AT allele[a] | 2.5 | 0.94 | 0.56 (0.54-0.59) |
| CFH CC vs. TT | 12.6 | 0.34 | 0.31 (0.23-0.38) |
| Smoking ≥10 pack-years or AT/AT (no del allele) or CFH CC[a] | 6.0 | 0.85 | 0.71 (0.66-0.76) |
| | | | |
| HTRA1 rs11200638 | | | |
| AA vs. GG | 98.4 | 0.32 | 0.32 (0.24-0.40) |
| AG vs. GG | 6.1 | 0.41 | 0.34 (0.27-0.41) |
| Smoking | | | |
| (<10 pack-years vs. ≥10 pack-years) | 4.1 | 0.54 | 0.41 (0.35-0.47) |
| Smoking ≥10 pack-years or A allele[a] | 4.1 | 0.87 | 0.66 (0.62-0.70) |
| CFH CC vs. TT | 19.6 | 0.34 | 0.32 (0.24-0.39) |
| Smoking ≥10 pack-years or A allele or CFH CC[a] | 10.7 | 0.91 | 0.82 (0.78-0.87) |
| | | | |
| HTRA1 rs2672598 | | | |
| CC vs. TT | 36.5 | 0.48 | 0.46 (0.38-0.55) |
| TC vs. TT | 4.3 | 0.41 | 0.32 (0.25-0.38) |
| Smoking | | | |
| (<10 pack-years vs. ≥10 pack-years) | 3.5 | 0.54 | 0.39 (0.33-0.45) |
| Smoking ≥10 pack-years or C allele[a] | 3.5 | 0.94 | 0.67 (0.64-0.70) |
| CFH CC vs. TT | 10.3 | 0.34 | 0.30 (0.23-0.38) |
| Smoking ≥10 pack-years or CC (no T allele) or CFH CC[a] | 8.0 | 0.86 | 0.75 (0.70-0.80) |

FIG. 6A

| Exposure | Relative Risk | Frequency in cases, θ | Adjusted PAR (95% Confidence Interval) |
|---|---|---|---|
| HTRA1 rs1049331 | | | |
| TT vs. CC | 105.5 | 0.33 | 0.33 (0.25-0.41) |
| TC vs. CC | 6.0 | 0.40 | 0.33 (0.26-0.40) |
| Smoking | | | |
| (<10 pack-years vs. ≥10 pack-years) | 4.1 | 0.54 | 0.41 (0.35-0.48) |
| Smoking ≥10 pack-years or T allele[a] | 4.1 | 0.87 | 0.66 (0.61-0.70) |
| CFH CC vs. TT | 19.3 | 0.34 | 0.32 (0.24-0.39) |
| Smoking ≥10 pack-years or T allele or CFH CC[a] | 10.7 | 0.91 | 0.82 (0.78-0.87) |
| HTRA1 rs2293870 | | | |
| CC, CT or TT vs. GG | 26.0 | 0.41 | 0.39 (0.31-0.47) |
| CG or TG vs. GG | 5.9 | 0.40 | 0.33 (0.26-0.40) |
| Smoking | | | |
| (<10 pack-years vs. ≥10 pack-years) | 3.3 | 0.54 | 0.38 (0.32-0.44) |
| Smoking ≥10 pack-years or C or T allele[a] | 3.4 | 0.90 | 0.64 (0.60-0.67) |
| CFH CC vs. TT | 13.9 | 0.34 | 0.31 (0.24-0.39) |
| Smoking ≥10 pack-years or C or T allele or CFH CC[a] | 8.0 | 0.94 | 0.82 (0.78-0.86) |

FIG. 6B

| Marker/SNP | Physical Location (bp) |
|---|---:|
| D10S1690 | 95984772 |
| D10S1230 | 122732682 |
| D10S1483 | 123273561 |
| PLEKHA1 rs1045216 | 124179187 |
| LOC387715 rs10490923 | 124204241 |
| LOC387715 rs2736911 | 124204345 |
| LOC387715 rs10490924 | 124204438 |
| LOC387715 rs10664316 | 124206376 |
| LOC387715 rs7088128 | 124206400 |
| HTRA1 rs11200638 | 124210534 |
| HTRA1 -602 from ATG$^a$ G>A | 124210557 |
| HTRA1 -502 from ATG$^a$ C>T | 124210657 |
| HTRA1 rs2672598 | 124210672 |
| HTRA1 rs1049331 | 124211260 |
| HTRA1 rs2293870 | 124211266 |
| HTRA1 rs12267142 | 124238232 |
| HTRA1 rs2239586 | 124239225 |
| HTRA1 rs2672582 | 124256490 |
| HTRA1 intron 5 (del GTTT) | 124256969-124256981 |
| HTRA1 rs2672583 | 124257077 |
| HTRA1 rs3013206 | 124257163 |
| HTRA1 rs2672585 | 124258391 |
| HTRA1 rs11538140 | 124261518 |
| HTRA1 rs2272599 | 124261585 |
| HTRA1 rs28689095 | 124261715 |
| HTRA1 rs2293871 | 124263661 |
| D10S587 | 125178595 |
| D10S1213 | 125356627 |
| D10S1723 | 125650839 |
| D10S1656 | 126091772 |
| D10S1222 | 129150739 |

FIG. 7

| Population | Mean Age | Range | Standard Deviation | % Male (n/134) |
|---|---|---|---|---|
| Affected Siblings | 71.28 | 48.97-86.38 | 8.26 | 45.5% (61/134) |
| Unaffected Siblings | 72.77 | 41.32-90.86 | 8.97 | 39.6% (53/134) |

FIG. 8

| Gene | Region | Forward Primer | Reverse Primer |
|---|---|---|---|
| PLEKHA1 putative | exon 12 | CTGACCGTGTCTGACTGCC (SEQ ID NO. 13) | CCCCTTATCATCTTTGGCTA (SEQ ID NO. 14) |
| LOC387715 putative | exon 1 | TTGTGTGACGGGAAAAGACA (SEQ ID NO. 15) | AAGCACCTGAAGGCTGGTTA (SEQ ID NO. 16) |
| LOC387715 | exon 2 | TTGTTACAAAAGGAATGGAATGTC (SEQ ID NO. 17) | GGAATGCAGTGACAGAGAGGA (SEQ ID NO. 18) |
| HTRA1 | promoter a | ATGCCACCCACACCAAGATTCTCC (SEQ ID NO. 19) | GGTTCTCGCTGAGATTCG (SEQ ID NO. 20) |
| HTRA1 | promoter b | CGGATGCACCAAAGATTCTCC (SEQ ID NO. 21) | TTCGCGTCCTTCAAACTAATGG (SEQ ID NO. 22) |
| HTRA1 | exon 1a | GAGGCCCTCCTGCACTCT (SEQ ID NO. 23) | CAGGTTGGCGTAGGTGTTG (SEQ ID NO. 24) |
| HTRA1 | exon 1b | GAGTCGCCATGCAGATCC (SEQ ID NO. 25) | CGAGCTGGGATGGAGAGA (SEQ ID NO. 26) |
| HTRA1 | exon 2 | AAACAAACTTGGGCCATCAG (SEQ ID NO. 27) | TTGCTAGTGGCGGTGAAAG (SEQ ID NO. 28) |
| HTRA1 | exon 3 | TAGGTGTGTGTGGCTGTTGC (SE ID NO. 29) | AAGTTTTCCTGAGCCCCTTC (SEQ ID NO. 30) |
| HTRA1 | exon 4 | CGCAGCAAAGGGATGTTAGT (SEQ ID NO. 31) | GAATCCACATGGCTTGGTCT (SEQ ID NO. 32) |
| HTRA1 | exon 5 | CCAGGCAGGGACATAGATTG (SEQ ID NO. 33) | TCAGCAGCCCAGGAGATTA (SEQ ID NO. 34) |
| HTRA1 | exon 6 | GGTGTCCTGATGCCTCTC (SEQ ID NO. 35) | TGCCATGATCAGAGGACAAA (SEQ ID NO. 36) |
| HTRA1 | exon 7 | GTCCAGACCAGGATTTGAGC (SEQ ID NO. 37) | CCAAGGCTAATGACCTGTCC (SEQ ID NO. 38) |
| HTRA1 | exon 8 | AGGAGAAGACGGGAACTGGT (SEQ ID NO. 39) | CTCGTGGAGCAAGGACTTT (SEQ ID NO. 40) |
| HTRA1 | exon 9/3'-UTR | CTGACCCACTGATGGTTTGA (SEQ ID NO. 41) | CTATTCCAGCAGCCCAGAGT (SEQ ID NO. 42) |

FIG. 9

| rs # | Gene | Region | Nucleotide Change | Amino Acid Change (If applicable) | Chromosome position (bp) | MAF (Unaffected) | Frequency in Affected |
|---|---|---|---|---|---|---|---|
| rs1045216 | PLEKHA1 | exon 12 | G>A | Thr320Ala | 124179187 | A = 0.291 | A = 0.254 |
| rs10490923 | LOC387715 | exon 1 | G>A | Arg3His | 124204241 | A = 0.108 | A = 0.060 |
| rs2736911 | LOC387715 | exon 1 | T>C | Arg38End | 124204345 | C = 0.097 | C = 0.086 |
| rs10490924 | LOC387715 | exon 1 | G>T | Ala69Ser | 124204438 | T = 0.328 | T = 0.526 |
| rs10664316 | LOC387715 | intron 1 | del AT | | 124206375^124206376 | - = 0.414 | - = 0.269 |
| rs7088128 | LOC387715 | intron 1 | A>G | | 124206400 | G = 0.119 | G = 0.067 |
| rs11200638 | HTRA1 | promoter | G>A | | 124210534 | A = 0.317 | A = 0.522 |
| | HTRA1 | promoter | G>A | | 124210557 | A = 0.022 | A = 0.015 |
| | HTRA1 | promoter | C>T | | 124210657 | T = 0.060 | T = 0.049 |
| rs2672598 | HTRA1 | promoter | C>T | | 124210672 | T = 0.496 | T = 0.321 |
| rs1049331 | HTRA1 | exon 1 | C>T | Ala34Ala | 124211260 | T = 0.317 | T = 0.526 |
| rs2293870 | HTRA1 | exon 1 | G>C[a] | Gly36Gly | 124211266 | C = 0.090 | C = 0.086 |
| | HTRA1 | | G>T | Gly36Gly | 124211266 | T = 0.317 | T = 0.522 |
| rs12267142[b] | HTRA1 | intron 1 | C>G | | 124238232 | G = 0.022 | G = 0.022 |
| rs2239586 | HTRA1 | intron 3 | C>T | | 124239225 | T = 0.108 | T = 0.078 |
| rs2239587 | HTRA1 | intron 3 | G>A | | 124239299 | A = 0.116 | A = 0.086 |
| rs2672582 | HTRA1 | intron 4 | C>T | | 124256490 | T = 0.429 | T = 0.507 |
| rs2672583 | HTRA1 | intron 5 | del GTTT | | 124256973^124256976 | - = 0.392 | - = 0.351 |
| rs3013206[b] | HTRA1 | intron 5 | G>A | | 124257077 | A = 0.422 | A = 0.515 |
| rs2672585 | HTRA1 | intron 5 | A>T | | 124257163 | T = 0.045 | T = 0.022 |
| rs11538140[b] | HTRA1 | intron 6 | C>G | | 124258391 | G = 0.425 | G = 0.507 |
| rs2672599 | HTRA1 | exon 8 | C>T | Asp407Asp | 124261518 | T = 0.004 | T = 0.004 |
| rs2293871 | HTRA1 | intron 8 | A>G | | 124261585 | G = 0.474 | G = 0.545 |
| | HTRA1 | intron 8 | C>T | | 124263661 | T = 0.138 | T = 0.101 |

FIG. 10

| LOC387715 rs10490924 | | Affected Siblings (Index cases) | | Unaffected Siblings | |
|---|---|---|---|---|---|
| | | Frequency % | No. | Frequency % | No. |
| | Genotype | | | | |
| | TT | 33.58 | 45 | 16.42 | 22 |
| | TG | 38.06 | 51 | 32.84 | 44 |
| | GG | 28.36 | 38 | 50.75 | 68 |
| | Total | | 134 | | 134 |
| | Allele | | | | |
| | T | 52.61 | 141 | 32.84 | 88 |
| | G | 47.39 | 127 | 67.16 | 180 |
| | Total | | 268 | | 268 |

| LOC387715 rs10664316 | | Affected Siblings (Index cases) | | Unaffected Siblings | |
|---|---|---|---|---|---|
| | | Frequency % | No. | Frequency % | No. |
| | Genotype | | | | |
| | -- | 11.19 | 15 | 18.66 | 25 |
| | --AT | 31.34 | 42 | 45.52 | 61 |
| | AT | 57.46 | 77 | 35.82 | 48 |
| | Total | | 134 | | 134 |
| | Allele | | | | |
| | -- | 26.87 | 72 | 41.42 | 111 |
| | AT | 73.13 | 196 | 58.58 | 157 |
| | Total | | 268 | | 268 |

| HTRA1 rs11200638 | | Affected Siblings (Index cases) | | Unaffected Siblings | |
|---|---|---|---|---|---|
| | | Frequency % | No. | Frequency % | No. |
| | Genotype | | | | |
| | AA | 32.09 | 43 | 15.67 | 21 |
| | AG | 40.30 | 54 | 32.09 | 43 |
| | GG | 27.61 | 37 | 52.2 | 70 |
| | Total | | 134 | | 134 |
| | Allele | | | | |
| | A | 52.24 | 140 | 31.72 | 85 |
| | G | 47.76 | 128 | 68.28 | 183 |
| | Total | | 268 | | 268 |

| HTRA1 rs2672598 | | Affected Siblings (Index cases) | | Unaffected Siblings | |
|---|---|---|---|---|---|
| | | Frequency % | No. | Frequency % | No. |
| | Genotype | | | | |
| | TT | 11.94 | 16 | 26.12 | 35 |
| | TC | 40.30 | 54 | 47.01 | 63 |
| | CC | 47.76 | 64 | 26.87 | 36 |
| | Total | | 134 | | 134 |
| | Allele | | | | |
| | T | 32.09 | 86 | 49.63 | 133 |
| | C | 67.91 | 182 | 50.37 | 135 |
| | Total | | 268 | | 268 |

FIG. 11A

| HTRA1 | | Affected Siblings (Index cases) | | Unaffected Siblings | |
|---|---|---|---|---|---|
| | | Frequency % | No. | Frequency % | No. |
| rs1049331 | Genotype | | | | |
| | TT | 32.84 | 44 | 15.67 | 21 |
| | TC | 39.55 | 53 | 32.09 | 43 |
| | CC | 27.61 | 37 | 52.24 | 70 |
| | Total | | 134 | | 134 |
| | Allele | | | | |
| | T | 52.61 | 141 | 31.72 | 85 |
| | C | 47.39 | 127 | 68.2 | 183 |
| | Total | | 268 | | 268 |

| HTRA1 | | Affected Siblings (Index cases) | | Unaffected Siblings | |
|---|---|---|---|---|---|
| | | Frequency % | No. | Frequency % | No. |
| rs2293870 | Genotype | | | | |
| | CC | 0.75 | 1 | 2.24 | 3 |
| | TT | 31.34 | 42 | 15.67 | 21 |
| | CG | 6.72 | 9 | 9.70 | 13 |
| | TG | 32.84 | 44 | 28.36 | 38 |
| | CT | 8.96 | 12 | 3.73 | 5 |
| | GG | 19.41 | 26 | 40.30 | 54 |
| | Total | | 134 | | 134 |
| | Allele | | | | |
| | C | 8.58 | 23 | 8.96 | 24 |
| | T | 52.23 | 140 | 31.72 | 85 |
| | G | 39.18 | 105 | 59.33 | 159 |
| | Total | | 268 | | 268 |

FIG. 11B

SEQUENCE LISTING

```
<160> NUMBER OF SEQ ID NOS: 42

<210> SEQ ID NO 1
<211> LENGTH: 41
<212> TYPE: DNA
<213> ORGANISM: Homo sapiens

<400> SEQUENCE: 1
ctgcccggcc cagtccgagc ytcccgggcg ggcccccagt c                           41

<210> SEQ ID NO 2
<211> LENGTH: 41
<212> TYPE: DNA
<213> ORGANISM: Homo sapiens

<400> SEQUENCE: 2 gactggggc ccgcccggga rgctcggact gggccgggca g                            41

<210> SEQ ID NO 3
<211> LENGTH: 41
<212> TYPE: DNA
<213> ORGANISM: Homo sapiens
<220> FEATURE:
<221> NAME/KEY: misc_feature
<222> LOCATION: (21)..(21)
<223> OTHER INFORMATION: Wherein n is presence of AT or deletion of AT

<400> SEQUENCE: 3
taaaatatcg tcatgtgtct nttaaaaatg catattacta a                           41

<210> SEQ ID NO 4
```

```
<211> LENGTH: 41
<212> TYPE: DNA
<213> ORGANISM: Homo sapiens
<220> FEATURE:
<221> NAME/KEY: misc_feature
<222> LOCATION: (21)..(21)
<223> OTHER INFORMATION: Wherein n is presence of TA or deletion of TA.

<400> SEQUENCE: 4
ttagtaatat gcattttaa nagacacatg acgatatttt a                    41

<210> SEQ ID NO 5
<211> LENGTH: 41
<212> TYPE: DNA
<213> ORGANISM: Homo sapiens

<400> SEQUENCE: 5
tcggcgcctt tggccgccgg btgcccagac cgctgcgagc c                   41

<210> SEQ ID NO 6
<211> LENGTH: 41
<212> TYPE: DNA
<213> ORGANISM: Homo sapiens

<400> SEQUENCE: 6
ggctcgcagc ggtctgggca vccggcggcc aaaggcgccg a                   41

<210> SEQ ID NO 7
<211> LENGTH: 41
<212> TYPE: DNA
<213> ORGANISM: Homo sapiens

<400> SEQUENCE: 7
ggccgctcgg cgcctttggc ygccgggtgc ccagaccgct g                   41

<210> SEQ ID NO 8
<211> LENGTH: 41
<212> TYPE: DNA
<213> ORGANISM: Homo sapiens

<400> SEQUENCE: 8
cagcggtctg ggcacccggc rgccaaaggc gccgagcggc c                   41

<210> SEQ ID NO 9
<211> LENGTH: 41
<212> TYPE: DNA
<213> ORGANISM: Homo sapiens

<400> SEQUENCE: 9
cacactccat gatcccagct kctaaaatcc acactgagct c                   41

<210> SEQ ID NO 10
<211> LENGTH: 41
<212> TYPE: DNA
<213> ORGANISM: Homo sapiens

<400> SEQUENCE: 10
gagctcagtg tggattttag magctgggat catggagtgt g                   41

<210> SEQ ID NO 11
<211> LENGTH: 41
<212> TYPE: DNA
<213> ORGANISM: Homo sapiens

<400> SEQUENCE: 11
```

-continued cgcggacgct gccttcgtcc rgccgcagag gccccgcggt c            41

<210> SEQ ID NO 12
<211> LENGTH: 41
<212> TYPE: DNA
<213> ORGANISM: Homo sapiens

<400> SEQUENCE: 12
gaccgcgggg cctctgcggc yggacgaagg cagcgtccgc g            41

<210> SEQ ID NO 13
<211> LENGTH: 19
<212> TYPE: DNA
<213> ORGANISM: Artificial Sequence
<220> FEATURE:
<223> OTHER INFORMATION: PLEKHA1 exon 12 Forward Primer Chemically
      Synthesized

<400> SEQUENCE: 13
ctgaccgtgt ctgactgcc                                     19

<210> SEQ ID NO 14
<211> LENGTH: 20
<212> TYPE: DNA
<213> ORGANISM: Artificial Sequence
<220> FEATURE:
<223> OTHER INFORMATION: PLEKHA1 exon 12 Reverse Primer Chemically
      Synthesized

<400> SEQUENCE: 14
ccccttatca tctttggcta                                    20

<210> SEQ ID NO 15
<211> LENGTH: 20
<212> TYPE: DNA
<213> ORGANISM: Artificial Sequence
<220> FEATURE:
<223> OTHER INFORMATION: LOC387715 exon 1 Forward Primer Chemically
      Synthesized

<400> SEQUENCE: 15
ttgtgtgacg ggaaaagaca                                    20

<210> SEQ ID NO 16
<211> LENGTH: 20
<212> TYPE: DNA
<213> ORGANISM: Artificial Sequence
<220> FEATURE:
<223> OTHER INFORMATION: LOC387715 exon Reverse Sequence Chemically
      Synthesized

<400> SEQUENCE: 16
aagcacctga aggctggtta                                    20

<210> SEQ ID NO 17
<211> LENGTH: 24
<212> TYPE: DNA
<213> ORGANISM: Artificial Sequence
<220> FEATURE:
<223> OTHER INFORMATION: LOC387715 exon 2 Forward Primer Chemically
      Synthesized

<400> SEQUENCE: 17
ttgttacaaa aggaatggaa tgtc                               24

<210> SEQ ID NO 18
<211> LENGTH: 21

```
<212> TYPE: DNA
<213> ORGANISM: Artificial Sequence
<220> FEATURE:
<223> OTHER INFORMATION: LOC387715 exon 2 Reverse Primer Chemically
      Synthesized

<400> SEQUENCE: 18
ggaatgcagt gacagagagg a                                                   21

<210> SEQ ID NO 19
<211> LENGTH: 20
<212> TYPE: DNA
<213> ORGANISM: Artificial Sequence
<220> FEATURE:
<223> OTHER INFORMATION: HTRA1 Promoter a Forward Primer Chemically
      Synthesized

<400> SEQUENCE: 19
atgccaccca caacaacttt                                                     20

<210> SEQ ID NO 20
<211> LENGTH: 20
<212> TYPE: DNA
<213> ORGANISM: Artificial Sequence
<220> FEATURE:
<223> OTHER INFORMATION: HTRA1 Promoter a Reverse Primer Chemically
      Synthesized

<400> SEQUENCE: 20
ggttctctcg ctgagattcg                                                     20

<210> SEQ ID NO 21
<211> LENGTH: 21
<212> TYPE: DNA
<213> ORGANISM: Artificial Sequence
<220> FEATURE:
<223> OTHER INFORMATION: HTRA1 Promoter b Forward Primer Chemically
      Synthesized

<400> SEQUENCE: 21
cggatgcacc aaagattctc c                                                   21

<210> SEQ ID NO 22
<211> LENGTH: 22
<212> TYPE: DNA
<213> ORGANISM: Artificial Sequence
<220> FEATURE:
<223> OTHER INFORMATION: HTRA1 Promoter b Reverse Primer Chemically
      Synthesized

<400> SEQUENCE: 22
ttcgcgtcct tcaaactaat gg                                                  22

<210> SEQ ID NO 23
<211> LENGTH: 18
<212> TYPE: DNA
<213> ORGANISM: Artificial Sequence
<220> FEATURE:
<223> OTHER INFORMATION: HTRA1 exon 1a Forward Primer Chemically
      Synthesized

<400> SEQUENCE: 23
gaggccctcc tgcactct                                                       18

<210> SEQ ID NO 24
<211> LENGTH: 19
<212> TYPE: DNA
<213> ORGANISM: Artificial Sequence
```

<220> FEATURE:
<223> OTHER INFORMATION: HTRA1 exon 1a Reverse Primer Chemically
      Synthesized

<400> SEQUENCE: 24
caggttggcg taggtgttg                                                  19

<210> SEQ ID NO 25
<211> LENGTH: 18
<212> TYPE: DNA
<213> ORGANISM: Artificial Sequence
<220> FEATURE:
<223> OTHER INFORMATION: HTRA1 exon 1b Forward Primer Chemically
      Synthesized

<400> SEQUENCE: 25
gagtcgccat gcagatcc                                                   18

<210> SEQ ID NO 26
<211> LENGTH: 18
<212> TYPE: DNA
<213> ORGANISM: Artificial Sequence
<220> FEATURE:
<223> OTHER INFORMATION: HTRA1 exon 1b Reverse Primer Chemically
      Synthesized

<400> SEQUENCE: 26
cgagctggga tggagaga                                                   18

<210> SEQ ID NO 27
<211> LENGTH: 20
<212> TYPE: DNA
<213> ORGANISM: Artificial Sequence
<220> FEATURE:
<223> OTHER INFORMATION: HTRA1 exon 2 Forward Primer Chemically
      Synthesized

<400> SEQUENCE: 27
aaacaaactt gggccatcag                                                 20

<210> SEQ ID NO 28
<211> LENGTH: 19
<212> TYPE: DNA
<213> ORGANISM: Artificial Sequence
<220> FEATURE:
<223> OTHER INFORMATION: HTRA1 exon 2 Reverse Primer Chemically
      Synthesized

<400> SEQUENCE: 28
ttgctagtgg cggtgaaag                                                  19

<210> SEQ ID NO 29
<211> LENGTH: 20
<212> TYPE: DNA
<213> ORGANISM: Artificial Sequence
<220> FEATURE:
<223> OTHER INFORMATION: HTRA1 exon 3 Forward Primer Chemically
      Synthesized

<400> SEQUENCE: 29
taggtgtgtg tggctgttgc                                                 20

<210> SEQ ID NO 30
<211> LENGTH: 20
<212> TYPE: DNA
<213> ORGANISM: Artificial Sequence
<220> FEATURE:
<223> OTHER INFORMATION: HTRA1 exon 3 Reverse Primer Chemically

```
                              Synthesized

<400> SEQUENCE: 30 aagtttcct gagcccttc                                                   20

<210> SEQ ID NO 31
<211> LENGTH: 20
<212> TYPE: DNA
<213> ORGANISM: Artificial Sequence
<220> FEATURE:
<223> OTHER INFORMATION: HTRA1 exon 4 Forward Primer Chemically
      Synthesized

<400> SEQUENCE: 31
cgcagcaaag ggatgttagt                                                 20

<210> SEQ ID NO 32
<211> LENGTH: 20
<212> TYPE: DNA
<213> ORGANISM: Artificial Sequence
<220> FEATURE:
<223> OTHER INFORMATION: HTRA1 exon 4 Reverse Primer Chemically
      Synthesized

<400> SEQUENCE: 32
gaatccacat ggcttggtct                                                 20

<210> SEQ ID NO 33
<211> LENGTH: 20
<212> TYPE: DNA
<213> ORGANISM: Artificial Sequence
<220> FEATURE:
<223> OTHER INFORMATION: HTRA1 exon 5 Forward Primer Chemically
      Synthesized

<400> SEQUENCE: 33
ccaggcaggg acatagattg                                                 20

<210> SEQ ID NO 34
<211> LENGTH: 20
<212> TYPE: DNA
<213> ORGANISM: Artificial Sequence
<220> FEATURE:
<223> OTHER INFORMATION: HTRA1 exon 5 Reverse Primer Chemically
      Synthesized

<400> SEQUENCE: 34
tcagcagccc aggagattta                                                 20

<210> SEQ ID NO 35
<211> LENGTH: 20
<212> TYPE: DNA
<213> ORGANISM: Artificial Sequence
<220> FEATURE:
<223> OTHER INFORMATION: HTRA1 exon 6 Forward Primer Chemically
      Synthesized

<400> SEQUENCE: 35
ggtgtcctga tgcctctctc                                                 20

<210> SEQ ID NO 36
<211> LENGTH: 20
<212> TYPE: DNA
<213> ORGANISM: Artificial Sequence
<220> FEATURE:
<223> OTHER INFORMATION: HTRA1 exon 6 Reverse Primer Chemically
      Synthesized
```

<400> SEQUENCE: 36
tgccatgatc agaggacaaa                                              20

<210> SEQ ID NO 37
<211> LENGTH: 20
<212> TYPE: DNA
<213> ORGANISM: Artificial Sequence
<220> FEATURE:
<223> OTHER INFORMATION: HTRA1 exon 7 Forward Primer Chemically
      Synthesized

<400> SEQUENCE: 37
gtccagacca ggatttgagc                                              20

<210> SEQ ID NO 38
<211> LENGTH: 20
<212> TYPE: DNA
<213> ORGANISM: Artificial Sequence
<220> FEATURE:
<223> OTHER INFORMATION: HTRA1 exon 7 Reverse Primer Chemically
      Synthesized

<400> SEQUENCE: 38
ccaaggctaa tgacctgtcc                                              20

<210> SEQ ID NO 39
<211> LENGTH: 20
<212> TYPE: DNA
<213> ORGANISM: Artificial Sequence
<220> FEATURE:
<223> OTHER INFORMATION: HTRA1 exon 8 Forward Primer Chemically
      Synthesized

<400> SEQUENCE: 39
aggagaagac gggaactggt                                              20

<210> SEQ ID NO 40
<211> LENGTH: 20
<212> TYPE: DNA
<213> ORGANISM: Artificial Sequence
<220> FEATURE:
<223> OTHER INFORMATION: HTRA1 exon 8 Reverse Primer Chemically
      Synthesized

<400> SEQUENCE: 40
ctcgtggagc aaggactttt                                              20

<210> SEQ ID NO 41
<211> LENGTH: 20
<212> TYPE: DNA
<213> ORGANISM: Artificial Sequence
<220> FEATURE:
<223> OTHER INFORMATION: HTRA1 exon 9/3'-UTR Forward Primer Chemically
      Synthesized

<400> SEQUENCE: 41
ctgacccact gatggtttga                                              20

<210> SEQ ID NO 42
<211> LENGTH: 20
<212> TYPE: DNA
<213> ORGANISM: Artificial Sequence

```
<220> FEATURE:
<223> OTHER INFORMATION: HTRA1 exon 9/3'-UTR Reverse Primer Chemically
      Synthesized

<400> SEQUENCE: 42
ctattccagc agcccagagt                                                    20
```

METHODS FOR DETECTING AGE-RELATED MACULAR DEGENERATION

RELATED APPLICATIONS

This application claims the benefit of and priority to U.S. Provisional Patent Application Ser. Nos. 60/890,339, filed Feb. 16, 2007, and 60/970,828, filed Sep. 7, 2007, the entire disclosure of each of which is incorporated by reference herein for all purposes.

GOVERNMENT FUNDING

The work described in this application was sponsored, in part, by the National Eye Institute under Grant No. EY-014458. The United States Government may have certain rights in the invention.

FIELD OF THE INVENTION

The invention relates generally to methods and compositions for determining whether an individual is at risk of developing age-related macular degeneration by detecting whether the individual has a protective or risk variant of the HTRA1 gene, and to methods and compositions for treating, or slowing the progression of, age-related macular degeneration by administering an agent that reduces the expression of the HTRA1 gene or reduces the biological activity of the HTRA1 gene product.

BACKGROUND

There are a variety of chronic intraocular disorders, which, if untreated, may lead to partial or even complete vision loss. One prominent chronic intraocular disorder is age-related macular degeneration, which is the leading cause of blindness amongst elderly Americans affecting a third of patients aged 75 years and older (Fine et al. (2000) NEW ENGL. J. MED. 342: 483-492). There are two forms of age-related macular degeneration, a dry form and a wet (also known as a neovascular) form.

The dry form involves a gradual degeneration of a specialized tissue beneath the retina, called the retinal pigment epithelium, accompanied by the loss of the overlying photoreceptor cells. These changes result in a gradual loss of vision. The wet form is characterized by the growth of new blood vessels beneath the retina which can bleed and leak fluid, resulting in a rapid, severe and irreversible loss of central vision in the majority cases. This loss of central vision adversely affects one's everyday life by impairing the ability to read, drive and recognize faces. In some cases, the macular degeneration progresses from the dry form to the wet form, and there are at least 200,000 newly diagnosed cases a year of the wet form (Hawkins et al. (1999) MOL. VISION 5: 26-29). The wet form accounts for approximately 90% of the severe vision loss associated with age-related macular degeneration.

At this time, current diagnostic methods cannot accurately predict the risk of age-related macular degeneration for an individual. Unfortunately, the degeneration of the retina has already begun by the time age-related macular degeneration is diagnosed in the clinic. Further, most current treatments are limited in their applicability, and are unable to prevent or reverse the loss of vision especially in the case of the wet type, the more severe form of the disease (Miller et al. (1999) ARCH. OPHTHALMOL. 117(9): 1161-1173).

Currently, the treatment of the dry form of age-related macular degeneration includes administration of antioxidant vitamins and/or zinc. Treatment of the wet form of age-related macular degeneration, however, has proved to be more difficult.

Several methods have been approved in the United States of America for treating the wet form of age-related macular degeneration. Two are laser based approaches, and include laser photocoagulation and photodynamic therapy using a benzoporphyrin derivative photosensitizer known as Visudyne. Two require the administration of therapeutic molecules that bind and inactivate or reduce the activity of Vascular Endothelial Growth Factor (VEGF), one is known as Lucentis (ranibizumab), which is a humanized anti-VEGF antibody fragment, and the other is known as Macugen (pegaptanib sodium injection), which is an anti-VEGF aptamer.

During laser photocoagulation, thermal laser light is used to heat and photocoagulate the neovasculature of the choroid. A problem associated with this approach is that the laser light must pass through the photoreceptor cells of the retina in order to photocoagulate the blood vessels in the underlying choroid. As a result, this treatment destroys the photoreceptor cells of the retina creating blind spots with associated vision loss.

During photodynamic therapy, a benzoporphyrin derivative photosensitizer known as Visudyne and available from QLT, Inc. (Vancouver, Canada) is administered to the individual to be treated. Once the photosensitizer accumulates in the choroidal neovasculature, non-thermal light from a laser is applied to the region to be treated, which activates the photosensitizer in that region. The activated photosensitizer generates free radicals that damage the vasculature in the vicinity of the photosensitizer (see, U.S. Pat. Nos. 5,798,349 and 6,225,303). This approach is more selective than laser photocoagulation and is less likely to result in blind spots. Under certain circumstances, this treatment has been found to restore vision in patients afflicted with the disorder (see, U.S. Pat. Nos. 5,756,541 and 5,910,510).

Lucentis, which is available from Genentech, Inc., CA, is a humanized therapeutic antibody that binds and inhibits or reduces the activity of VEGF, a protein believed to play a role in angiogenesis. Pegaptanib sodium, which is available from OSI Pharmaceuticals, Inc., NY, is a pegylated aptamer that targets VEGF165, the isoform believed to be responsible for primary pathological ocular neovascularization.

Despite these efforts, there is still an ongoing need for methods of identifying individuals at risk of developing age-related macular degeneration so that such individuals can be monitored more closely and then treated to slow, stop or reverse the onset of age-related macular degeneration. In addition, there is still an ongoing need for new methods of preventing the onset of age-related macular degeneration, and, once established, the treatment of age-related macular degeneration.

SUMMARY

The invention is based, in part, upon the discovery of protective and risk variants of the High Temperature Requirement Serine Peptidase 1 (HTRA1) gene. In one aspect, a protective variant C>T (rs2672598) in the HTRA1 gene was identified that is associated with reduced risk of the neovascular form of age-related macular degeneration (AMD). Individuals homozygous for the protective allele T (TT) (p<0.0001) have a 33-fold lower risk of developing neovascular AMD, whereas individuals heterozygous for the protective allele T (TC) (p<0.001) have a 8-fold lower risk of developing neovascular AMD when compared to individuals homozygous for the common allele C (CC).

In another aspect, a protective variant, a deletion of AT (rs10664316) in LOC387715, which is upstream from the HTRA1 gene, was identified that is associated with decreased risk of developing the neovascular form of AMD. Individuals homozygous for the deletion of AT (delAT/delAT) (p<0.001) have an 11-fold reduced risk of developing neovascular AMD, whereas individuals heterozygous for the deletion of AT (delAT/AT) (p<0.01) have a 3-fold reduced risk of developing neovascular AMD when compared to individuals homozygous for the common alleles (AT/AT).

In another aspect, a risk variant C>T (rs1049331) in exon 1 of the HTRA1 gene was identified that is associated with increased risk of developing the neovascular form of AMD. Individuals homozygous for the risk allele T (TT) (p<0.00001) have a 106-fold higher risk of developing neovascular AMD, whereas individuals heterozygous for the risk allele T (TC) (p<0.001) have a 6-fold higher risk of developing neovascular AMD when compared to individuals homozygous for the common allele C (CC).

Additionally, another risk variant G>C/T (rs2293870) in exon 1 of the HTRA1 gene was identified that is associated with increased risk of developing the neovascular form of AMD. Individuals homozygous for the risk allele T/C (TT, CC, or CT) (p<0.00001) have a 26-fold higher risk of developing neovascular AMD, whereas individuals heterozygous for the risk allele T/C (TG or CG) (p<0.01) have a 6-fold higher risk of developing neovascular AMD when compared to individuals homozygous for the common allele G (GG).

Accordingly, in one aspect, the invention provides a method of determining a subject's, for example, a human subject's, risk of developing age-related macular degeneration. The method comprises determining whether the subject has a variant at a polymorphic site of the HTRA1 gene or upstream from the HTRA1 gene (e.g. 5' to the gene and its regulatory regions, LOC387715), such as a protective variant or a risk variant. If the subject has at least one protective variant, the subject is less likely to develop age-related macular degeneration than a person without the protective variant. There are two exemplary protective variants. One is located in the promoter region of the HTRA1 gene, and the other one is located upstream from the HTRA1 gene. If the subject has at least one risk variant, the subject is more likely to develop age-related macular degeneration than a person without the risk variant. Two exemplary risk variants are both located in exon 1 of the HTRA1 gene.

The method can further comprise determining the genotypes at one or more of the polymorphic sites. In certain embodiments, the method can include determining the genotype at rs2672598. If the subject is heterozygous for the protective variant T at rs2672598, the subject has a 8-fold lower risk of developing age-related macular degeneration. If the subject is homozygous for the protective variant T at rs2672598, the subject has a 33-fold lower risk of developing age-related macular degeneration. In certain embodiments, the method can include determining the genotype at rs10664316. If the subject is heterozygous for the protective variant, deletion of AT (delAT) at rs10664316, the subject has a 3-fold lower risk of developing age-related macular degeneration. If the subject is homozygous for the protective variant, deletion of AT (delAT) at rs10664316, the subject has an 11-fold lower risk of developing age-related macular degeneration. In certain embodiments, the method can include determining the genotype at rs1049331. If the subject is heterozygous for the risk allele T at rs1049331, the subject has a 6-fold higher risk of developing AMD. If the subject is homozygous for the risk allele T at rs1049331, the subject has a 106-fold higher risk of developing AMD. In certain embodiments, the method can include determining the genotype at rs2293870. If the subject is heterozygous for the risk allele T/C at rs2293870, the subject has a 6-fold higher risk of developing AMD. If the subject is homozygous for the risk allele T/C at rs2293870, the subject has a 26-fold higher risk of developing AMD.

In certain embodiments, the protective variant is a single nucleotide polymorphism: rs2672598, located in the upstream region of the HTRA1 gene.
For example, the forward sequence comprises CTGCCCGGCCCAGTCCGAGCX$_1$TCCCGGGCGGGCC CCCAGTC (SEQ ID NO. 1) wherein X$_1$ is a C to T substitution. C is the common allele, and T is the protective variant. Alternatively, the reverse sequence comprises GACTGGGGGCCCGCCCGGGAX$_2$GCTCGGACTGGG CCGGGCAG (SEQ ID NO. 2) wherein X$_2$ is a G to A substitution. G is the common allele, and A is the protective variant.

In another embodiment, the protective variant is a deletion/insertion polymorphism: rs10664316, located within LOC387715, which is upstream from the HTRA1 gene.
For example, the forward sequences comprises TAAAATATCGTCATGTGTCTX$_3$TTAAAAATGCATATT ACTAA (SEQ ID NO. 3) wherein X$_3$ is a change of presence of AT to deletion of AT. The presence of AT is the common allele, and the deletion of AT is the protective variant.
Alternatively, the reverse sequence comprises TTAGTAATATGCATTTTTAAX$_4$AGACACATGACGATA TTTTA (SEQ ID NO. 4) wherein X$_4$ is a change of presence of TA to deletion of TA. The presence of TA is the common allele, and the deletion of TA is the protective variant.

In certain embodiments, the risk variant is a single nucleotide polymorphism: rs2293870 (HTRA1 Gly36Gly). For example, the forward sequence comprises TCGGCGCCTTTGGCCGCCGGX$_5$TGCCCAGACCGCT GCGAGCC (SEQ ID NO. 5) wherein X$_5$ is a G to a C or T substitution. G is the common allele, and C or T is the risk variant.
Alternatively, the reverse sequence comprises GGCTCGCAGCGGTCTGGGCAX$_6$CCGGCGGCCAAA GGCGCCGA (SEQ ID NO. 6) wherein X$_6$ is a C to a G or A substitution. C is the common allele, and G or A is the risk variant. rs2293870 is a synonymous single nucleotide polymorphism with a G to a C or U substitution in the forward sequence or a C to a G or A substitution in the reverse sequence at HTRA1 mRNA position 220, coding for a Gly residue at corresponding amino acid position 36.

In certain embodiments, the risk variant is a single nucleotide polymorphism: rs1049331 (HTRA1 Ala34Ala). For example, the forward sequence comprises GGCCGCTCGGCGCCTTTGGCX$_7$GCCGGGTGCCCA GACCGCTG (SEQ ID NO. 7) wherein X$_7$ is a C to T substitution. C is the common allele, and T is the risk variant.
Alternatively, the reverse sequence comprises CAGCGGTCTGGGCACCCGGCX$_8$GCCAAAGGCGCC AGCGGCC (SEQ ID NO. 8) wherein X$_8$ is a G to A substitution. G is the common allele, and A is the risk variant. rs1049331 is a synonymous single nucleotide polymorphism with a C to a U substitution in the forward sequence or a G to an A substitution in the reverse sequence at HTRA1 mRNA position 214, coding for an Ala residue at corresponding amino acid position 34.

In certain embodiments, the risk variant is a single nucleotide polymorphism: rs10490924 (LOC387715 Ala69Ser). For example, the forward sequence comprises CACACTCCATGATCCCAGCTX$_9$CTAAAATCCACACT GAGCTC (SEQ ID NO. 9) wherein X$_9$ is a G to T substitution. G is the common allele, and T is the risk variant. Alternatively, the reverse sequence comprises GAGCTCAGTGTGGATTTTAGX$_{10}$AGCTGGGATCATG GAGTGTG (SEQ ID NO. 10) wherein X$_{10}$ is a C to A substitution. C is the common allele, and A is the risk variant. rs10490924 is a non-synonymous single nucleotide polymorphism with a G to a U substitution in the forward sequence or a C to an A substitution in the reverse sequence at LOC387715 mRNA position 270, coding for an Ala to a Ser substitution at corresponding amino acid position 69.

In certain embodiments, the risk variant is a single nucleotide polymorphism: rs11200638, located in the upstream region of HTRA1 gene. For example, the forward sequence comprises CGCGGACGCTGCCTTCGTCCX$_{11}$GCCGCAGAGGCC CCGCGGTC (SEQ ID NO. 11) wherein X$_{11}$ is a G to A substitution. G is the common allele, and A is the risk variant. Alternatively, the reverse sequence comprises GACCGCGGGGCCTCTGCGGCX$_{12}$GGACGAAGGCAG CGTCCGCG (SEQ ID NO. 12) wherein X$_{12}$ is a C to T substitution. C is the common allele, and T is the risk variant.

According to ENSEMBL, the above-identified single nucleotide polymorphisms appear in the following order from 5' to 3': rs10490924, rs10664316, rs11200638, rs2672598, rs1049331, rs2293870 (see, for example, the web site at www.ensembl.org).

The variant (e.g. the genotype at a polymorphic site) can be determined by standard techniques known in the art, which can include, for example, direct nucleotide sequencing, hybridization assays using a probe that anneals to the protective variant, to the risk variant, or to the common allele at the polymorphic site, restriction fragment length polymorphism assays, or amplification-based assays. Furthermore, it is contemplated that the polymorphic sites may be amplified prior to the detection steps. In certain embodiments, the genotype may be determined by an amplification reaction using primers capable of amplifying the polymorphic site.

In another aspect, the invention provides a method of treating, slowing the progression of, or reversing the development of age-related macular degeneration in a subject, for example, a human subject. The method comprises (i) reducing the expression of the HTRA1 gene or (ii) reducing the biological activity of the HTRA1 gene product.

The expression of the HTRA1 gene can be reduced by administering to the subject, for example, a human subject, an amount of, for example, an anti-sense polynucleotide or an siRNA effective to reduce the expression of the HTRA1 gene. Alternatively, the expression of the HTRA1 gene can be reduced by administering to the subject, an amount of an agent effective to modulate binding of the transcription factor, ELK-1, to the promoter of the HTRA1 gene thereby reducing the expression of the HTRA1 gene. Alternatively, the biological activity of the HTRA1 gene product can be reduced by, for example, administering to the subject an effective amount of a binding protein that binds to the HTRA1 gene product to reduce the activity of the HTRA1 gene product. Exemplary compounds include anti-HTRA1 antibodies. Alternatively, the proteolytic activity of the HTRA1 gene product can be reduced by administering to the subject, an amount of an agent effective to modulate binding of the insulin-like growth factor, IGF, to the IGF-binding domain at the N-terminal end of the HTRA1 protein, thereby reducing the biological activity of the HTRA1 gene product.

In another aspect, the invention provides a method of determining a subject's, for example, a human subject's, risk of developing age-related macular degeneration. The method comprises determining whether the subject has a haplotype comprising two or more polymorphic sites selected from the group consisting of rs10490924, rs10664316, rs11200638, rs2672598, rs2293870, and rs1049331. If the subject has a risk haplotype, the subject is more likely to develop AMD than a subject without the haplotype. The haplotype can include rs10490924 as the risk variant, being T in its forward sequence, rs10664316 as the common allele, being the presence of AT in its forward sequence, rs11200638 as the risk variant, being A in its forward sequence, rs2672598 as the common allele, being C in its forward sequence, and/or rs1049331 as the risk variant, being T in its forward sequence. If the subject has the protective haplotype, the subject is less likely to develop AMD than a subject without the haplotype. The haplotype can include rs10490924 as the common allele, being G in its forward sequence, rs10664316 as the protective variant, being the deletion of AT in its forward sequence, rs11200638 as the common allele, being G in its forward sequence, rs2672598 as the protective variant, being T in its forward sequence, and/or rs1049331 as the common allele, being C in its forward sequence. Alternatively, or in addition, the reverse sequence can be used for this analysis. Determination of the haplotype can be through the use of any of the techniques described for determining the genotype above or below.

The foregoing aspects and embodiments of the invention may be more fully understood by reference to the following detailed description and claims.

BRIEF DESCRIPTION OF THE DRAWINGS

FIG. 2 shows single marker analysis results from a family-based association test (FBAT), assuming an additive genetic model. SNP represents single nucleotide polymorphism; **** refers to the fact that the number of informative families was less than 4 and that no statistics were available; PW p value represents point wise p values; FW p value represents family wise p values (Bonferroni correction was applied on 29 tests). $^a$ refers to the first coding ATG. Minor allele frequency was ≧5% in both affected and unaffected siblings.

FIG. 3 displays the identity by state scores, or the number (0, 1, or 2) of alleles shared between a set of sibling pairs for microsatellite markers. # refers to number; na represents non-applicable; h represents heterozygocity; Chi-sq represents Chi-squared statistic; p* represents p values that were adjusted by using the Bonferroni correction on eight tests. Significantly associated marker D10S1656 is located 1.8 Mb from the end of HTRA1 gene.

FIG. 4 shows the haplotype analysis results from a family based association test (FBAT). h1 represents haplotype 1; SNP represents single nucleotide polymorphism; p-value results were calculated based on 100,000 permutations. $^a$ refers to the first coding ATG. Estimated haplotypes with allele frequency greater than 0.05 were listed and tested for association. The resulting p value from 100,000 permutations was 0.00006 when all possible haplotypes were considered together. All SNPs were sequenced in all subjects in the forward direction, and additional confirmation was obtained by sequencing in the reverse direction in a small number of subjects carrying the risk alleles.

FIG. 5 shows the results of multiple conditional logistic regression analysis for six SNPs considered as risk factors for the development of AMD (rs10490924, rs10664316, rs1200638, rs2672598, rs1049331, and rs2293870). The Odds Ratios and p values are displayed as well. All SNPs were sequenced in all subjects in the forward direction, and additional confirmation was obtained by sequencing in the reverse direction in a small number of subjects carrying the risk alleles.

FIGS. 6A and 6B show the results of population attributable risk (PAR) analysis for six SNPs considered as risk factors for the development of AMD (rs10490924, rs10664316, rs11200638, rs2672598, rs1049331, and rs2293870). Relative risk was estimated by conditional logistic regression analysis adjusting for other factors. The relative risk value was less than the sum of the adjusted PARs, because these risk factors were not mutually exclusive, and the relative risk used here was not adjusting for other factors. All SNPs were sequenced in all subjects in the forward direction, and additional confirmation was obtained by sequencing in the reverse direction in a small number of subjects carrying the risk alleles.

FIG. 7 shows the location of microsatellite markers and SNPs. bp represents base pairs. $^a$ refers to the first coding ATG. The chromosome position of each microsatellite marker was determined by using a program available at the web site, compgen.rutgers.edu/mapomat/. The chromosome position of each SNP was determined by using a program available at the web site, www.ensembl.org/Homo_sapiens/geneview?gene=ENSG00000166033.

FIG. 8 shows the characteristics of the subjects in the two analyzed groups: affected siblings and unaffected siblings. The characteristics include the range of the ages of the subjects, the mean age, the standard deviation of the distribution of the ages and the percentage of males in any one of the two groups.

FIG. 9 shows the primers used in the studies described herein. Primers are written in the 5'-3' direction and were chosen using the Primer3 program (available at the web site, www.primer3.sourceforge.net) to encompass the entire coding region and flanking intronic sequences.

FIG. 10 describes the SNPs analyzed in the studies described herein. bp represents base pairs; MAF represents Minor Allele Frequency. The chromosome position of each SNP was determined by using a program available at the web site, www.ensembl.org/Homo_sapiens/geneview?gene=ENSG00000166033. $^a$ refers to the most minor allele of the three alleles; $^b$ refers to variants/SNPs excluded from statistical analysis because Minor Allele Frequency (MAF) did not meet the criteria of ≧5% in both unaffected and affected siblings. All SNPs were sequenced in all subjects in the forward direction, and additional confirmation was obtained by sequencing in the reverse direction in a small number of subjects carrying the risk alleles.

FIGS. 11A and 11B show the genotypes and allele frequencies of six SNPs analyzed in the studies described herein for two groups: affected siblings and unaffected siblings. All SNPs were sequenced in all subjects in the forward direction, and additional confirmation was obtained by sequencing in the reverse direction in a small number of subjects carrying the risk alleles.

DETAILED DESCRIPTION

Figure 1:
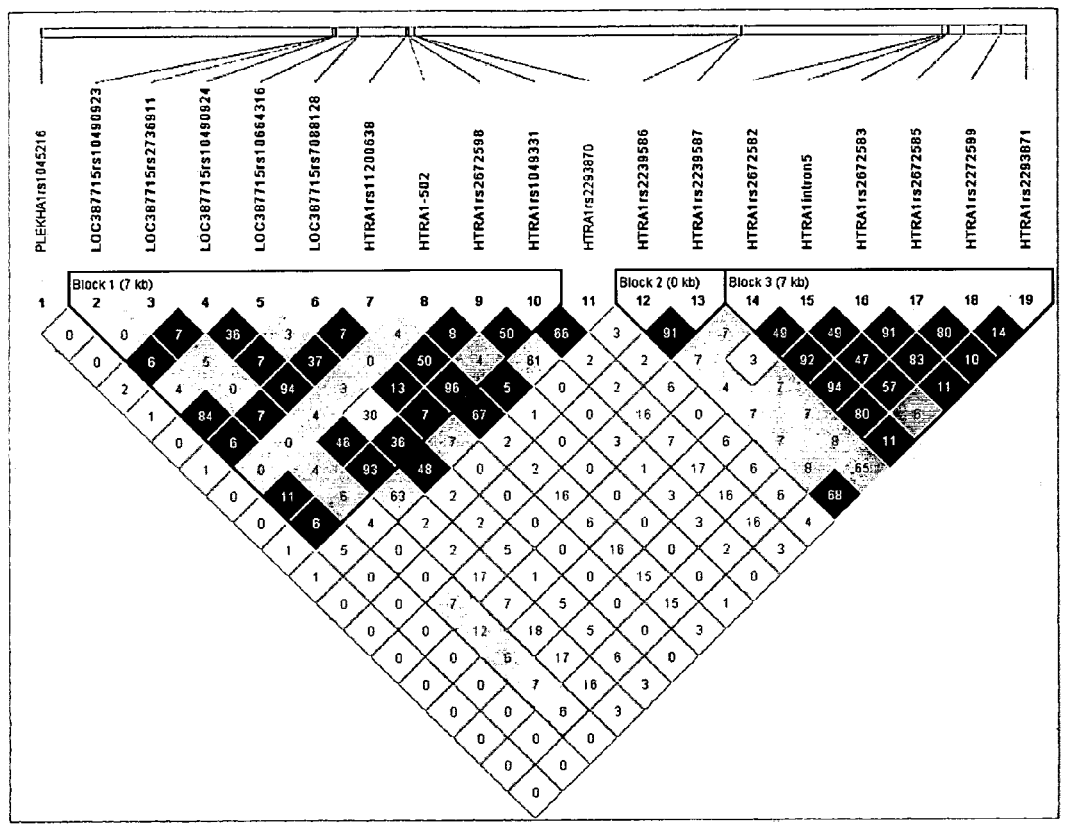
FIG. 1 shows a display of linkage disequilibrium ($r^2$) between the genotyped SNPs in the genes PLEKHA1, LOC387715 and HTRA1. ENSEMBL SNPs are shown along the 10q26 region encompassing PLEKHA1, LOC387715 and HTRA1, illustrating the three distinct haplotype blocks, which were defined by the confidence intervals using an algorithm proposed by Gabriel (Gabriel, S. B. et al. The structure of haplotype blocks in the human genome. *Science* (2002) 296, 2225-2229) using HAPLOVIEW. The linkage disequilibrium ($r^2$) between any two SNPs is listed in the cross cell. The darker the color in the display, the higher the linkage disequilibrium between any two SNPs.

As discussed previously, the invention is based, in part, upon the discovery of two protective and two risk variants at polymorphic sites of the HTRA1 gene or upstream from the HTRA1 gene (e.g. 5' to the gene and regulatory regions; LOC387715). Two protective variants, C>T (rs2672598) in the HTRA1 gene and presence of AT>deletion of AT (rs10664316) in LOC387715, which is upstream from the HTRA1 gene, have been found to be associated with reduced risk of developing the neovascular form of age-related macular degeneration (AMD). Individuals homozygous for the protective allele T (TT) of rs2672598 (p<0.0001) have a 33-fold lower risk of developing neovascular AMD, whereas individuals heterozygous for the protective allele T (TC) of rs2672598 (p<0.001) have a 8-fold lower risk of developing neovascular AMD when compared to those homozygous for the common allele C (CC) of rs2672598. Individuals homozygous for the protective variant, deletion of AT (delAT) (delAT/delAT) of rs10664316 (p<0.001), have an 11-fold lower risk of developing neovascular AMD, whereas individuals heterozygous for the protective variant, deletion of AT (delAT) (delAT/AT) of rs10664316 (p<0.01), have a 3-fold lower risk of developing neovascular AMD when compared to those homozygous for the common alleles (AT/AT) of rs10664316.

Two risk variants, C>T (rs1049331) and G>C/T (rs2293870), have been found to be associated with increased risk of developing the neovascular form of AMD. Individuals homozygous for the risk allele T (TT) of rs1049331 (p<0.00001) have a 106-fold higher risk of developing neovascular AMD, whereas individuals heterozygous for the risk allele T (TC) of rs1049331 (p<0.001) have a 6-fold higher risk of developing neovascular AMD when compared to individuals homozygous for the common allele C (CC) of rs1049331. Individuals homozygous for the risk allele T/C (TT, CC, or CT) of rs2293870 (p<0.00001) have a 26-fold higher risk of developing neovascular AMD, whereas individuals heterozygous for the risk allele T/C (TG or CG) of rs2293870 (p<0.01) have a 6-fold higher risk of developing neovascular AMD when compared to individuals homozygous for the common allele G (GG) of rs2293870.

Although the Single Nucleotide Polymorphisms (SNPs), rs2672598, rs10664316, rs2293870 and rs10049331 are known, their associations with the risk of developing neovascular AMD heretofore were not known. HTRA1 is a heat shock protein that encodes a serine protease that is believed to indirectly regulate insulin. One protective variant at rs2672598 is located in the promoter region of HTRA1, and the other protective variant at rs10664316 is located within LOC387715, which is upstream from the HTRA1 gene, both of which are near two other variants (present in SNPs rs10490924 and rs1200638) that have recently been reported to be associated with an increased risk of AMD. The two risk variants at rs2293870 and rs1049331 are both located in exon 1 of HTRA1 gene. rs1049331 is located between rs2672598 and rs2293870: 588 bp downstream of rs2672598 and 6 bp upstream of rs2293870.

In vivo (DeWan et al. (2006) SCIENCE 314: 989-992) and in vitro studies (Yang et al. (2006) SCIENCE 314-992-993) of HTRA1 have shown that SNP rs11200638, increases the risk of developing AMD, most likely doing so by upregulating the expression of the HTRA1 gene. This SNP appears to reside in the binding sites for serum response factor. The increased risk of developing AMD is believed to relate to an increased expression of the HTRA1 gene.

Using the computer program MapInspector, located on the world wide web at the web site, www.genomatrix.de/, rs2672598 was identified as being located in the binding site for the transcription factor ELK-1. The protective allele of rs2672598 appears to create a binding site for the transcription factor ELK-1. It is contemplated that the variant at this SNP alters the binding capacity of ELK-1 to the promoter region of HTRA1 to decrease or down regulate the expression of the HTRA1 gene.

In a recent clinical report of a patient with Metageria (an accelerated form of early aging) and insulin resistance it was postulated that ELK-1 activity was impaired or non functional (Knebel B. et al. (2005) EXP. CLIN. ENDOCRINOL. DIABETES, 113(2):94-101). Specifically in vitro assays on cultured fibroblasts from this patient demonstrated that not only were the insulin receptors functioning properly but that the pathways activated by insulin were working properly as well. The authors concluded that the insulin resistance in this prematurely aging patient was most likely due to improper phosphorylation of ELK-1, which resulted in this transcription factor not being able to function at all. Insulin resistance or the body's inability to regulate insulin properly underlies diabetes. A 10-year prospective study year showed that diabetes was associated with increased risk of neovascular age-related macular degeneration (AREDS Report No. 19, 2005 OPHTHALMOL.). Without wishing to be bound by theory, it is contemplated that the variant at rs2672598 facilitates the proper binding of ELK-1 thereby down regulating the expression of the HTRA1 gene and helping to keep levels of insulin in the body to a normal level.

SNP rs2293870 is located in one of the HTRA1 binding domains for insulin-like growth factors (IGFs). IGF has been implicated in other ocular conditions characterized by neovascularization such as diabetic retinopathy and retinopathy of prematurity. Binding of HTRA1 may directly modulate IGF expression. For example, in studies of patients who progress from non-proliferative diabetic retinopathy to neovascularization (proliferative diabetic retinopathy) patient serum and vitreal IGF levels were found to be significantly elevated (Shaw and Grant (2004) Reviews in Endocrine & Metabolic Disorders 5: 199-207).

Therefore, an effect of rs2293870 on a regulatory pathway involving HTRA1 and IGFs has biologic plausibility for AMD. For example, improper regulation or expression of IGF may result in cell death—apoptosis, such as, death of the photoreceptors (Shaw and Grant (2004) Reviews in Endocrine & Metabolic Disorders 5: 199-207). Additionally, the nucleotide change at rs2293870 may generate an alternative splice site in the HTRA1 transcript.

I. Prognosis and Diagnosis of Neovascular AMD

In one aspect, the invention provides a method of determining a subject's, for example, a human subject's, risk of developing age-related macular degeneration. The method comprises determining whether the subject has a protective variant at a polymorphic site of the HTRA1 gene or in a region upstream from the HTRA1 gene wherein, if the subject has at least one protective variant, the subject is less likely to develop age-related macular degeneration than a person without the protective variant. One exemplary protective variant is at a SNP, rs2672598, located in the promoter region of the HTRA1 gene. For example, the forward sequence comprises CTGCCCGGCCCAGTCCGAGCX$_1$TCCCGGGCGGGC CCCCAGTC (SEQ ID NO. 1) wherein $X_1$ is a C to T substitution. C is the common allele and T is the protective variant. Alternatively, the reverse sequence comprises GACTGGGGGCCCGCCCGGGAX$_2$GCTCGGACTGGG CCGGGCAG (SEQ ID NO. 2) wherein $X_2$ is a G to A substitution. G is the common allele and A is the protective variant.

Another exemplary protective variant is at a SNP, rs10664316, located within LOC387715, which is upstream from the HTRA1 gene. For example, the forward sequence comprises TAAAATATCGTCATGTGTCTX$_3$TTAAAAA TGCATATTACTAA (SEQ ID NO. 3) wherein $X_3$ is a change of presence of AT to deletion of AT. The presence of AT is the common allele, and the deletion of AT is the protective variant. Alternatively, the reverse sequence comprises TTAGTAATATGCATTTTTAAX$_4$AGACACATGACGATA TTTTA (SEQ ID NO. 4) wherein $X_4$ is a change of presence of TA to deletion of TA. The presence of TA is the common allele, and the deletion of the TA is the protective variant.

In another aspect, the invention provides a method of determining a subject's, for example, a human subject's, risk of developing age-related macular degeneration. The method comprises determining whether the subject has a risk variant at a polymorphic site of the HTRA1 gene, wherein, if the subject has at least one risk variant, the subject is more likely to develop age-related macular degeneration than a person without the risk variant. One exemplary risk variant is at a SNP, rs2293870, located in exon 1 of the HTRA1 gene. For example, the forward sequence comprises TCGGCGCCTTTGGCCGCCGGX$_5$TGCCCAGACCGCT GCGAGCC (SEQ ID NO. 5) wherein $X_5$ is a G to C or T substitution. G is the common allele and T or C is the risk variant. Alternatively, the reverse sequence comprises GGCTCGCAGCGGTCTGGGCAX$_6$CCGGCGGCCAAAG GCGCCGA (SEQ ID NO. 6) wherein $X_6$ is a C to a G or A substitution. C is the common allele and G or A is the risk variant. rs2293870 is a synonymous single nucleotide polymorphism with a G to a C or U substitution in the forward sequence or a C to a G or A substitution in the reverse sequence at HTRA1 mRNA position 220, coding for a Gly residue at corresponding amino acid position 36.

Another exemplary risk variant is at a SNP, rs1049331, located in exon 1 (6 bp upstream of rs2293870) of the HTRA1 gene. For example, the forward sequence comprises GGCCGCTCGGCGCCTTTGGCX$_7$GCCGGGTGCCCAG ACCGCTG (SEQ ID NO. 7) wherein $X_7$ is a C to T substitution. C is the common allele and T is the risk variant. Alternatively, the reverse sequence comprises CAGCGGTCTGGGCACCCGGCX$_8$GCCAAAGGCGCCG AGCGGCC (SEQ ID NO. 8) wherein $X_8$ is a G to an A substitution. G is the common allele and A is the risk variant. rs1049331 is a synonymous single nucleotide polymorphism with a C to a U substitution in the forward sequence or a G to an A substitution in the reverse sequence at HTRA1 mRNA position 214, coding for an Ala residue at corresponding amino acid position 34.

The presence of a protective and/or risk variant can be determined by standard nucleic acid detection assays including, for example, conventional SNP detection assays, which may include, for example, amplification-based assays, probe hybridization assays, restriction fragment length polymorphism assays, and/or direct nucleic acid sequencing. Exemplary protocols for preparing and analyzing samples of interest are discussed in the following sections.

A. Preparation of Samples for Analysis

Polymorphisms can be detected in a target nucleic acid samples from an individual under investigation. In general, genomic DNA can be analyzed, which can be selected from any biological sample that contains genomic DNA or RNA. For example, genomic DNA can be obtained from peripheral blood leukocytes using standard approaches (QIAamp DNA Blood Maxi kit, Qiagen, Valencia, Calif.). Nucleic acids can be harvested from other samples, for example, cells in saliva, cheek scrapings, skin or tissue biopsies, amniotic fluid. Methods for purifying nucleic acids from biological samples suitable for use in diagnostic or other assays are known in the art.

B. Detection of Polymorphisms in Target Nucleic Acids

The identity of bases present at the polymorphic sites, rs2672598, rs2293870 and rs1049331, in the HTRA1 gene, and rs10664316, upstream from the HTRA1 gene, can be determined in an individual using any of several methods known in the art. The polymorphisms can be detected by direct sequencing, amplification-based assays, probe hybridization-based assays, restriction fragment length polymorphism assays, denaturing gradient gel electrophoresis, single-strand conformation polymorphism analyses, and denaturing high performance liquid chromatography. Other methods to detect nucleic acid polymorphisms include the use of: Molecular Beacons (see, e.g., Piatek et al. (1998) NAT. BIOTECHNOL. 16:359-63; Tyagi and Kramer (1996) NAT. BIOTECHNOL. 14:303-308; and Tyagi et al. (1998) NAT. BIOTECHNOL. 16:49-53), the Invader assay (see, e.g., Neri et al. (2000) ADV. NUCL. ACID PROTEIN ANALYSIS 3826: 117-125 and U.S. Pat. No. 6,706,471), and the Scorpion assay (Thelwell et al. (2000) NUCL. ACIDS RES. 28:3752-3761 and Solinas et al. (2001) NUCL. ACIDS RES. 29:20).

The design and use of allele-specific probes for analyzing polymorphisms are described, for example, in EP 235,726, and WO 89/11548. Briefly, allele-specific probes are designed to hybridize to a segment of target DNA from one individual but not to the corresponding segment from another individual, if the two segments represent different polymorphic forms. Hybridization conditions are chosen that are sufficiently stringent so that a given probe essentially hybridizes to only one of two alleles. Typically, allele-specific probes are designed to hybridize to a segment of target DNA such that the polymorphic site aligns with a central position of the probe.

The design and use of allele-specific primers for analyzing polymorphisms are described, for example, in WO 93/22456. Briefly, allele-specific primers are designed to hybridize to a site on target DNA overlapping a polymorphism and to prime DNA amplification according to standard PCR protocols only when the primer exhibits perfect complementarity to the particular allelic form. A single-base mismatch prevents DNA amplification and no detectable PCR product is formed. The method works particularly well when the polymorphic site is at the extreme 3'-end of the primer, because this position is most destabilizing to elongation from the primer.

The primers, once selected, can be used in standard PCR protocols in conjunction with another common primer that hybridizes to the upstream non-coding strand of the HTRA1 gene at a specified location upstream from the polymorphism (or to the upstream non-coding strand of LOC387715 at a specific location upstream from the polymorphism). The common primers are chosen such that the resulting PCR products can vary from about 100 to about 300 bases in length, or about 150 to about 250 bases in length, although smaller (about 50 to about 100 bases in length) or larger (about 300 to about 500 bases in length) PCR products are possible. The length of the primers can vary from about 10 to 30 bases in length, or about 15 to 25 bases in length.

In addition, individuals with the protective variant can also be identified by restriction fragment length polymorphism (RFLP) assays. It is understood that in the presence of a protective variant at rs2672598, the C to T substitution results in the creation of a site of cleavage for the restriction endonuclease, AluI. In contrast to the common allele, which is not recognized by AluI, the protective allele can be detected by genotyping the individual by RFLP analysis.

Many of the methods for detecting polymorphisms involve amplifying DNA or RNA from target samples (e.g., amplifying the segments of the HTRA1 gene of an individual using HTRA1-specific primers, or amplifying segments of LOC387715 of an individual using LOC387715-specific primers) and analyzing the amplified gene segments. This can be accomplished by standard polymerase chain reaction (PCR & RT-PCR) protocols or other methods known in the art. Amplification products generated using PCR can be analyzed by the use of denaturing gradient gel electrophoresis. Different alleles can be identified based on sequence-dependent melting properties and electrophoretic migration in solution. See Erlich, ed., PCR Technology, Principles and Applications for DNA Amplification, Chapter 7 (W.H. Freeman and Co, New York, 1992).

SNP detection can also be accomplished by direct PCR amplification, for example, via Allele-Specific PCR (AS-PCR) which is the selective PCR amplification of one of the alleles to detect Single Nucleotide Polymorphism (SNP). Selective amplification is usually achieved by designing a primer such that the primer will match/mismatch one of the alleles at the 3'-end of the primer. The amplifying may result in the generation of HTRA1 allele-specific oligonucleotides, which span any of the SNPs, rs2672598, rs2293870 or rs1049331, or in the generation of LOC387715 allele-specific oligonucleotides, which may span rs10664316. The HTRA1-specific (or LOC387715-specific) primer sequences and HTRA1 allele-specific (or LOC387715 allele-specific) oligonucleotides may be derived from the coding (exons) or non-coding (promoter, 5' untranslated, introns or 3' untranslated) regions of the HTRA1 gene (or of LOC387715).

Direct sequencing analysis of polymorphisms can be accomplished using DNA sequencing procedures known in the art. See Sambrook et al., Molecular Cloning, A Laboratory Manual (2nd Ed., CSHP, New York 1989) and Zyskind et al., Recombinant DNA Laboratory Manual (Acad. Press, 1988).

A wide variety of other methods are known in the art for detecting polymorphisms in a biological sample. See, e.g., U.S. Pat. No. 6,632,606; Shi (2002) AM. J. PHARMACOGENOMICS 2:197-205; Kwok et al. (2003) CURR. ISSUES BIOL. 5:43-60). Detection of the single nucleotide polymorphic form (i.e., the presence or absence of the variant at rs2672598, rs10664316, rs2293870 or rs1049331), alone and/or in combination with each other and/or in combination with additional HTRA1 gene polymorphisms and/or LOC387715 polymorphisms, may increase the probability of an accurate diagnosis. In one embodiment, screening involves determining the presence or absence of the variant at rs2672598. In another embodiment, screening involves determining the presence or absence of the variant at rs2293870. In another embodiment, screening involves determining the presence or absence of the variant at rs1049331. In another embodiment, screening involves determining the presence or absence of the variant at rs10664316.

In diagnostic methods, the analysis of rs2672598, rs10664316, rs2293870 and/or rs1049331 can be combined with each other and/or can be combined with analysis of polymorphisms in other genes associated with AMD, detection of protein markers of AMD (see, e.g., U.S. Patent Application Publication Nos. US2003/0017501 and US2002/0102581 and International Application Publication Nos. WO184149 and WO106262), assessment of other risk factors of AMD (such as family history), with ophthalmological examination, and with other assays and procedures.

Screening also can involve detecting a haplotype which includes two or more SNPs. Such SNPs include those described herein and/or additional HTRA1 gene polymorphisms and/or LOC387715 polymorphisms, and/or other gene associated with AMD and/or other risk factors. The SNPs include, but are not limited to, rs10490924, rs10664316, rs11200638, rs2672598, rs2293870, and rs1049331. For the two or more SNPs, one determines if the risk variant is present or absent (for risk variant SNPs) and/or if the common allele is present or absent (for protective variant SNPs) in order to diagnose a subject for being at increased risk of developing AMD. Conversely, for the two or more SNPs, one can determine if the common allele is present or absent (for risk variant SNPs) and/or the protective variant is present or absent (for protective variant SNPs) in order to diagnose a subject for being at reduced risk of developing AMD. If the subject has a haplotype in the forward direction of T(AT)ACT at rs10490924, rs10664316, rs11200638, rs2672598, and rs1049331, respectively, the subject has an increased risk of developing AMD relative to a person without the haplotype ($p<10^{-4}$). If the subject has a haplotype in the forward direction of G(delAT)GTC at rs10490924, rs10664316, rs1200638, rs2672598, and rs1049331, respectively, the subject has a reduced risk of developing AMD relative to a person without the haplotype ($p<10^{-2}$).

II. Treatment of Neovascular AMD

In another aspect, the invention provides a method of treating, slowing the progression of, or reversing the development of age-related macular degeneration in a subject, for example, a human subject. The method comprises (i) reducing the expression of the HTRA1 gene or (ii) reducing the biological activity of the HTRA1 gene product.

The expression of the HTRA1 gene can be reduced by administering to the subject an amount of an agent effective to reduce the expression of the HTRA1 gene. Examples include, for example, an anti-sense polynucleotide or a siRNA effective to reduce the expression of the HTRA1 gene. Specific examples include, for example, siRNA (1900si) (Chien et al., (2006), J CLIN INVEST. 116(7): 1994-2004), sc-60083 (Santa Cruz Biotechnology, Inc., Santa Cruz, Calif.), and sc-43854 (Santa Cruz Biotechnology, Inc., Santa Cruz, Calif.).

Alternatively, the expression of the HTRA1 gene can be reduced by administering to the subject, an amount of an agent effective to modulate binding of ELK-1 to the promoter of the HTRA1 gene thereby reducing the expression of the HTRA1 gene. Examples include, for example, short ELK-1 (sELK) (Vanhoutte et al. (2001) J BIOL CHEM. 276(7): 5189-96)

Alternatively, the expression of the HTRA1 gene product can be reduced by administering to the subject, an agent effective to increase the phosphorylation of ELK-1 then increase the activity of the ELK-1 gene product thereby reducing the expression of the HTRA1 gene. Examples include, for example, Silibinin (Sigma-Aldrich, St. Louis, Mo.), Dihydrotestosterone (DHT) (Sigma-Aldrich, St. Louis, Mo.), and/or 17β-estradiol ($E_2$) (Innovative Research of America, Sarasota, Fla.).

Alternatively, the proteolytic activity of the HTRA1 gene product can be reduced by administering to the subject an amount of an agent effective to modulate binding of the insulin-like growth factor, IGF, to the IGF-binding domain at the N-terminal end of the HTRA1 protein thereby reducing the biological activity of the HTRA1 gene product. Binding of HTRA1 may directly modulate IGF expression. For example, in studies of patients who progress from non-proliferative diabetic retinopathy to neovascularization (proliferative diabetic retinopathy) patient serum and vitreal IGF levels were found to be significantly elevated (Shaw and Grant (2004) Reviews in Endocrine & Metabolic Disorders 5: 199-207).

Alternatively, the expression of IGF can be modulated, for example, by administering to the subject an effective amount of agent to increase or reduce the expression level of IGF. For example, PTEN (phosphatase and tensin homolog) can downregulate IGF transcription (Kang-Park et al. (2003) FEBS Lett, 545(2-3): 203-208).

Alternatively, the biological activity of the HTRA1 gene product can be reduced, for example, by administering to the subject an effective amount of an agent that binds to the HTRA1 gene product to reduce the activity of the HTRA1 gene product. Exemplary compounds include proteins, for example, antibodies that bind to the HTRA1 gene product. Exemplary proteins include, for example, an anti-HTRA1 antibody. The term antibody is understood to mean an intact antibody, an antigen binding fragment thereof (for example, Fab, Fab' and $(Fab')_2$ fragments) and single chain antibody binding sites or sFvs.

Selective HTRA1 antagonists can also include peptides and peptide derivatives, which may be administered to systemically or locally to the mammal. Other useful selective HTRA1 antagonists include, for example, deoxyribonucleic acids (for example, antisense oligonucleotides), ribonucleic acids (for example, antisense oligonucleotides, aptamers, and interfering RNA) and peptidyl nucleic acids, which once administered reduce or eliminate the expression of certain genes (such as the HTRA1 gene) or can bind to and reduce or eliminate the activity of a target protein or receptor as in the case of aptamers. Other useful selective HTRA1 antagonists include small organic or inorganic molecules that reduce or eliminate the activity when administered to the mammal. Examples include, for example, NVP-LBG976, (Novartis, Basel), and 1-{3-cyclohexyl-2-[(naphthalene-2-carbonyl)-amino]-propionyl}-pyrrolidine-2-carboxylic acid [5-(3-cyclohexyl-ureido)-1-dihydroxyboranyl-pentyl]-amide (Novartis).

Once appropriate selective HTRA1 antagonists have been identified, they may be administered to a mammal of interest (such as a human) in any one of a wide variety of ways. It is contemplated that a selective HTRA1 antagonist can be administered either alone or in combination with two, three, four or more different selective HTRA1 antagonists either together or one after the other. Although the optimal mode of administration of a particular selective HTRA1 antagonist or combination of selective HTRA1 antagonists can be determined empirically, it is contemplated that selective HTRA1 antagonists may be administered locally or systemically.

Systemic modes of administration include both oral and parenteral routes. Parenteral routes include, for example, intravenous, intrarterial, intramuscular, intradermal, subcutaneous, intranasal, and intraperitoneal routes. It is contemplated that selective HTRA1 antagonists administered systemically may be modified or formulated to target the selective HTRA1 antagonist to the eye. Local modes of administration include, for example, intraocular, intraorbital, subconjuctival, intravitreal, subretinal or transcleral routes. It is noted, however, that local routes of administration are preferred over systemic routes because significantly smaller amounts of the selective HTRA1 antagonist can exert an effect when administered locally (for example, intravitreally) versus when administered systemically (for example, intravenously). Furthermore, the local modes of administration can reduce or eliminate the incidence of potentially toxic side effects that may occur when therapeutically effective amounts of a selective HTRA1 antagonist (i.e., an amount of a selective HTRA1 antagonist sufficient to reduce (for example, by 20%, 30%, 40%, 50%, 60%, 70%, 80%, 90%, or 95%) the biological activity or expression of HTRA1) are administered systemically.

Administration may be provided as a periodic bolus (for example, intravenously or intravitreally) or as continuous infusion from an internal reservoir (for example, from an implant disposed at an intra- or extra-ocular location (see, U.S. Pat. Nos. 5,443,505 and 5,766,242)) or from an external reservoir (for example, from an intravenous bag). The selective HTRA1 antagonist may be administered locally, for example, by continuous release from a sustained release drug delivery device immobilized to an inner wall of the eye or via targeted transscleral controlled release into the choroid (see, for example, PCT/US00/00207, PCT/US02/14279, Ambati et al. (2000) INVEST. OPHTHALMOL. VIS. SCI. 41:1181-1185, and Ambati et al. (2000) INVEST. OPHTHALMOL. VIS.SCI. 41:1186-1191). A variety of devices suitable for administering a selective HTRA1 antagonist locally to the inside of the eye are known in the art. See, for example, U.S. Pat. Nos. 6,251,090, 6,299,895, 6,416,777, 6,413,540, and 6,375,972, and PCT/US00/28187.

The selective HTRA1 antagonist also may be administered in a pharmaceutically acceptable carrier or vehicle so that administration does not otherwise adversely affect the recipient's electrolyte and/or volume balance. The carrier may comprise, for example, physiologic saline or other buffer system.

In addition, it is contemplated that the selective HTRA1 antagonist may be formulated so as to permit release of the selective HTRA1 antagonist over a prolonged period of time. A release system can include a matrix of a biodegradable material or a material which releases the incorporated selective HTRA1 antagonist by diffusion. The selective HTRA1 antagonist can be homogeneously or heterogeneously distributed within the release system. A variety of release systems may be useful in the practice of the invention; however, the choice of the appropriate system will depend upon the rate of release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that selective HTRA1 antagonists having different molecular weights are released by diffusion through or degradation of the material.

Representative synthetic, biodegradable polymers include, for example: polyamides such as poly(amino acids) and poly (peptides); polyesters such as poly(lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly(ethylene oxide), poly (ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

One of the primary vehicles currently being developed for the delivery of ocular pharmacological agents is the poly (lactide-co-glycolide) microsphere for intraocular injection. The microspheres are composed of a polymer of lactic acid and glycolic acid, which are structured to form hollow spheres. These spheres can be approximately 15-30 µm in diameter and can be loaded with a variety of compounds varying in size from simple molecules to high molecular weight proteins such as antibodies. The biocompatibility of these microspheres is well established (see, Sintzel et al. (1996) EUR. J. PHARM. BIOPHARM. 42: 358-372), and microspheres have been used to deliver a wide variety of pharmacological agents in numerous biological systems. After injection, poly(lactide-co-glycolide) microspheres are hydrolyzed by the surrounding tissues, which cause the release of the contents of the microspheres (Zhu et al. (2000) NAT. BIOTECH. 18: 52-57). As will be appreciated, the in vivo half-life of a microsphere can be adjusted depending on the specific needs of the system.

The type and amount of selective HTRA1 antagonist administered may depend upon various factors including, for example, the age, weight, gender, and health of the individual to be treated, as well as the type and/or severity of glaucoma to be treated. As with the modes of administration, it is contemplated that the optimal selective HTRA1 antagonists and dosages of those selective HTRA1 antagonists may be determined empirically.

By way of example, protein-, peptide- or nucleic acid-based selective HTRA1 antagonists can be administered at doses ranging, for example, from about 0.001 to about 500 mg/kg, optionally from about 0.01 to about 250 mg/kg, and optionally from about 0.1 to about 100 mg/kg. Nucleic acid-based selective HTRA1 antagonists may be administered at doses ranging from about 1 to about 20 mg/kg daily. Furthermore, antibodies that are selective HTRA1 antagonists may be administered intravenously at doses ranging from about 0.1 to about 5 mg/kg once every two to four weeks. With regard to intravitreal administration, the selective HTRA1 antagonists, for example, antibodies, may be administered periodically as boluses in dosages ranging from about 10 µg to about 5 mg/eye, and optionally from about 100 µg to about 2 mg/eye. With regard to transscleral administration, the selective HTRA1 antagonists may be administered periodically as boluses in dosages ranging from about 0.1 µg to about 1 mg/eye, and optionally from about 0.5 µg to about 0.5 mg/eye.

The present invention, therefore, includes the use of a selective HTRA1 antagonists in the preparation of a medicament for treating neovascular AMD. The selective HTRA1 antagonist or antagonists may be provided in a kit which optionally may comprise a package insert with instructions for how to treat the patient with, or at risk of developing, neovascular AMD. For each administration, the selective HTRA1 antagonist may be provided in unit-dosage or multiple-dosage form.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

In light of the foregoing description, the specific non-limiting examples presented below are for illustrative purposes and not intended to limit the scope of the invention in any way.

EXAMPLES

Example 1

Variants in the HTRA1 Gene Alter the Risk of Neovascular AMD

This Example describes the elucidation of alleles either conferring protection to, or increasing the risk of, the development of AMD.

Reports have not been in agreement as to which common variants in the chromosome10q26 region increase risk of developing AMD, the most common cause of blindness in those over age 50. Twenty-three SNPs were studied in the PLEKHA1/LOC387715/HTRA1 region in 134 extremely discordant sibpairs (268 subjects) where one member had neovascular AMD. Data from this cohort identified several significant variants in this region, including genotypes that reduced risk of developing AMD. Many SNPs, including the previously identified variants rs10490924 and rs1200638, defined two significant haplotypes associated with increased risk of developing neovascular AMD. The coding HTRA1 SNP rs2293870, not part of the significant haplotypes containing rs10490924 and rs1200638, showed a strong association with neovascular AMD susceptibility. Independent of the complement factor H (CFH) gene Y402H genotype (a variant of which has been identified as a risk factor for AMD) or smoking history, an individual's risk of developing AMD could be increased or decreased depending on their genotype or haplotype in the 10q26 region.

Wet or neovascular AMD is characterized by the growth of abnormal new blood vessels beneath the retina that can cause severe and rapid vision loss due to hemorrhage and exudation. It is this more advanced form that is responsible for the majority of debilitating vision loss due to AMD. In the U.S., it is predicted that about three million individuals over the age of 50 years will have advanced AMD in at least one eye by 2020.

Methods have yet to be refined that determine which individuals are at highest risk of vision loss due to advanced AMD prior to the development of any signs of the disease. The identification of allelic variants or biomarkers can help to predict risk of the more advanced stages of AMD. Although the CFH Y402H variant on 1q32 appears to be the most consistently associated genetic risk factor with AMD (Klein, R. J. et al. Complement factor H polymorphism in age-related macular degeneration. *Science* (2005) 308, 385-389; Edwards, A. O. et al. Complement factor H polymorphism and age-related macular degeneration. *Science* (2005) 308, 421-424; Haines, J. L. et al. Complement factor H variant increases the risk of age-related macular degeneration. *Science* (2005) 308, 419-421; Zareparsi, S. et al. Strong Association of the Y402H Variant in Complement Factor H at 1q32 with Susceptibility to Age-Related Macular Degeneration. *Am. J. Hum. Genet.* (2005) 77; Hageman, G. S. et al. A common haplotype in the complement regulatory gene factor H (HF1/CFH) predisposes individuals to age-related macular degeneration. *Proc. Natl. Acad. Sci.* (2005) U.S.A 102[20], 7227-7232), the 10q26 region where the genes PLEKHA1, LOC387715, HTRA1 reside adjacent to one another (FIG. 7), appears to be the most strongly associated overall with AMD susceptibility (Fisher, S. A. et al. Meta-analysis of genome scans of age-related macular degeneration. *Hum. Mol. Genet.* (2005) 14, 2257-2264). While many reports have demonstrated that variant rs10490924 in hypothetical LOC387715 is associated with all types of AMD (Jakobsdottir, J. et al. Susceptibility genes for age-related maculopathy on chromosome 10q26. *Am. J. Hum. Genet.* (2005) 77[389], 407; Rivera, A. et al. Hypothetical LOC387715 is a second major susceptibility gene for age-related macular degeneration, contributing independently of complement factor H to disease risk. *Hum. Mol. Genet.* (2005) 14, 3227-3236; Schmidt. S. et al. Cigarette smoking strongly modifies the association of LOC387715 and age-related macular degeneration. *Am. J. Hum. Genet.* (2006) 78, 852-864; Conley, Y. P. et al. CFH, ELOVL4, PLEKHA1 and LOC387715 genes and susceptibility to age-related maculopathy: AREDS and CHS cohorts and meta-analyses. *Hum. Mol. Genet.* (2006) 15, 3206-3218), it was recently shown that SNP rs11200638 in the HTRA1 promoter region, in linkage disequilibrium (LD) with rs10490924, was likely the causal variant (Dewan, A. et al. HTRA1 promoter polymorphism in wet age-related macular degeneration. *Science* (2006) 314, 989-992; Yang, Z. et al. A variant of the HTRA1 gene increases susceptibility to age-related macular degeneration. *Science* (2006) 314, 992-993; Cameron, D. J. et al. HTRA1 variant confers similar risks to geographic atrophy and neovascular age-related macular degeneration. *Cell Cycle* (2007) 6, 1122-1125). Moreover, data from the Age Related Eye Disease Study (AREDS) showed a significant association between SNP rs1045216 in PLEKHA1 and increased risk of developing neovascular AMD (Conley, Y. P. et al. CFH, ELOVL4, PLEKHA1 and LOC387715 genes and susceptibility to age-related maculopathy: AREDS and CHS cohorts and meta-analyses. *Hum. Mol. Genet.* (2006) 15, 3206-3218).

A phenotypically well defined cohort of extremely discordant sibpairs was used in the study presented here (Risch, N. & Zhang, H. Extreme discordant sib pairs for mapping quantitative trait loci in humans. *Science* (1995) 268, 1584-1589) to identify the contribution that allelic risk factors such as those reported in the 10q26 region make independently, and in combination with, the factors most consistently associated with AMD susceptibility: CFH Y402H genotype (Klein, R. J. et al. Complement factor H polymorphism in age-related macular degeneration. *Science* (2005) 308, 385-389; Edwards, A. O. et al. Complement factor H polymorphism and age-related macular degeneration. *Science* (2005) 308, 421-424; Haines, J. L. et al. Complement factor H variant increases the risk of age-related macular degeneration. *Science* (2005) 308, 419-421; Zareparsi, S. et al. Strong Association of the Y402H Variant in Complement Factor H at 1q32 with Susceptibility to Age-Related Macular Degeneration. *Am. J. Hum. Genet.* (2005) 77; Hageman, G. S. et al. A common haplotype in the complement regulatory gene factor H (HF1/CFH) predisposes individuals to age-related macular degeneration. *Proc. Natl. Acad. Sci.* (2005) U.S.A 102[20], 7227-7232) and smoking (Thornton, J. et al. Smoking and age-related macular degeneration: a review of association. *Eye* (2005) 19, 935-944).

Although the SNPs are known, their associations with risk of developing any type of age-related macular degeneration heretofore have not been determined. It is believed that no other protective variants have been identified in this gene. When smoking history and Complement Factor H (CFH) were included in the model with any of these variants, the significance and effect size were not modified with respect to the risk of developing age-related macular degeneration.

HTRA1 is a heat shock protein that encodes a serine protease that is purported to indirectly regulate insulin. The protective variant at rs2672598 identified in the study is located in the promoter region of HTRA1, near two other variants (at rs10490924 and rs11200638) that have recently been reported to be associated with increased risk of developing AMD. The results from the study presented here also confirmed these observations. Additionally, there are two risk variants, at rs2293870 and rs1049331, that are both located in exon 1 of the HTRA1 gene. rs1049331 is located between rs2672598 and rs2293870: 588 bp downstream of rs2672598 and 6 bp upstream of rs2293870.

Results

Thirty-three megabases of the 10q26 region (FIG. 7) were genotyped in samples from 134 unrelated patients with neovascular AMD (AREDS Scale, level 4b) who had one sibling with normal maculae and was past the age at which the affected sibling was diagnosed with neovascular AMD (AREDS Scale, level 0-1) (FIG. 8 and Methods) (Davis, M. D. et al. The Age-Related Eye Disease Study severity scale for age-related macular degeneration: AREDS Report No. 17. *Arch. Ophthalmol.* (2005) 123, 1484-1498). A combination of direct sequencing and analysis of eight highly polymorphic microsatellite markers tightly linked to the genes of interest (See Methods) was used to validate previous findings and possibly identify novel variants in the 10q26 region. For each of the 268 Caucasian subjects, all over the age of 50 years, exon 12 of PLEKHA1, the entire putative coding region of LOC387715, and the promoter region and entire coding region of HTRA1 were directly sequenced. All primer pairs were designed to encompass exon/intron boundaries (FIG. 9 and Methods).

Twenty-three variants were identified including deletions. Only the SNPs that had a minor allele frequency of ≧5% in both affected and unaffected siblings were used for statistical analysis (n=19) (FIG. 10). Six SNPs showed significant association with AMD risk after applying a Bonferonni correction from the results of the family based association test (FBAT) (FIG. 2). Genotype and allele frequencies for each of these SNPs are given in FIGS. 11A and 11B. No significant deviations from Hardy-Weinberg equilibrium for any of the variants studied were observed in either affected or unaffected siblings, indicating unlikely data contamination. FBAT demonstrated that the variant most strongly associated with AMD risk was a synonymous change in exon 1 of HTRA1, triallelic SNP (rs2293870) ($P<10^{-4}$), which, prior to this study, had not been shown to be associated with the risk of developing AMD. Additionally, novel significant associations with AMD susceptibility for an intronic deletion in hypothetical locus LOC387715, SNP rs10664316 ($P<10^{-3}$), the HTRA1 promoter SNP rs2672598 ($P<10^{-2}$), and another synonymous HTRA1 SNP, rs1049331 ($P<10^{-3}$), (FIG. 2) were identified. In agreement with others, FBAT demonstrated that SNPs rs10490924 ($P<10^{-3}$) and rs11200638 ($P<10^{-3}$) were significantly associated with AMD risk while no significant association was observed between neovascular AMD and PLEKHA1 (Dewan, A. et al. HTRA1 promoter polymorphism in wet age-related macular degeneration. *Science* (2006) 314, 989-992; Yang, Z. et al. A variant of the HTRA1 gene increases susceptibility to age-related macular degeneration. *Science* (2006) 314, 992-993). Except for SNP rs2293870, all significant SNPs were part of the same haplotype block as depicted in the linkage disequilibrium ($r^2$) plot in FIG. 1. SNP rs10490924 was in high LD with HTRA1 SNPs rs11200638 and rs1049331 ($r^2>0.90$). Although intronic SNP rs10664316 was not in high linkage disequilibrium with any other SNPs ($r^2<0.50$) examined, this did not preclude it from being a biomarker that in fact could be biologically associated with AMD susceptibility (Greally, J. M. Genomics: Encyclopaedia of humble DNA. *Nature* (2007) 447, 782-783; The ENCODE Project Consortium, Identification and analysis of functional elements in 1% of the human genome by the ENCODE pilot project. *Nature* (2007) 447, 799-816). Linkage analysis supported the findings of SNP association, as identity-by-state (IBS) scores calculated for each of the eight highly heterozygous microsatellite markers analyzed in this region demonstrated that D10S1656 was significantly associated with neovascular AMD ($P<10^{-15}$) (FIG. 3 and Methods).

FBAT demonstrated that two haplotypes (h2 and h6) in the 10q26 region were significantly associated with AMD risk (FIG. 4). SNPs rs10490924, rs10664316, rs11200638, rs2672598 and rs1049331 were more strongly associated with increased AMD risk as part of the most significant haplotype, h2 ($P<10^{-4}$), than when examined individually in FBAT analysis (FIG. 2).

Multiple conditional logistic regression (CLR) analyses were conducted to determine how each of the six significant SNPs contributed to the risk of neovascular AMD while adjusting for CFH Y402H genotype and smoking and, moreover, to examine if interactions existed between each SNP, CFH and/or smoking (FIG. 3). For each significant SNP, models were created to examine the minor allele in unaffected siblings in both the homozygous and heterozygous states versus having the common allele in the homozygous state. When smoking and CFH were included in each model with any of the significant variants, the significance and effect size were not modified with respect to AMD risk. Multiple CLR demonstrated that the most significantly associated variants with increased AMD risk were HTRA1 SNPs rs11200638 (AA vs. GG: OR: 98.41; CI: 13.45, 720.08; $p<10^{-5}$; AG vs. GG: OR: 6.05; CI: 2.13, 17.21; $p<10^{3}$) and rs1049331 (TT vs. CC: OR: 105.52; CI: 14.64, 760.5; $p<10^{-5}$; TC vs CC: OR: 5.97; CI: 2.10, 16.99; $p<10^{-3}$). Multiple CLR demonstrated that variants associated with increased risk of developing AMD were rs10490924 (TT vs. GG: OR: 61.91; CI: 10.89, 352.01; $p<10^{-5}$; TG vs. GG: OR: 5.32; CI: 1.82, 15.52; $p<10^{-2}$) and rs2293870 (CC, CT or TT vs. GG: OR: 25.97; CI: 6.32, 106.66; $p<10^{-5}$; CG or TG vs. GG: OR: 5.89; CI: 1.96, 17.71; $p<10^{-2}$). Multiple CLR also demonstrated that the variants associated with reduced risk of developing AMD were rs10664316 (delAT/delAT vs. AT/AT: OR: 0.09; CI: 0.02, 0.36; $p<10^{-3}$; delAT/AT vs. AT/AT: OR: 0.30; CI: 0.13, 0.72; $p<10^{-2}$), and rs2672598 (TT vs. CC: OR: 0.03; CI: 0.01, 0.14; $p<10^{-4}$; TC vs. CC: OR: 0.12; CI: 0.04, 0.39; $p<10^{-3}$). The HTRA1 SNP rs2672598 conferred a 33-fold reduced risk of developing AMD homozygously ($p<10^{-4}$) and 8-fold heterozygously ($p<10^{-3}$). The HTRA1 SNP rs1049331 conferred a 106-fold increased risk of developing AMD homozygously ($p<10^{-5}$) and 6-fold heterozygously ($p<10^{-3}$). The HTRA1 SNP rs2293870 conferred a 26-fold increased risk of developing AMD homozygously ($p<10^{-5}$) and 6-fold heterozygously ($p<10^{-2}$), (FIG. 5). The minor alleles in the homozygous state when compared to the common alleles in the homozygous state for SNPs rs10490924, rs11200638, rs1049331, rs2672598, and rs2293870, more strongly influenced AMD risk than the CFH Y402H C allele in the homozygous state (vs. TT). As previously reported (DeAngelis, M. M. et al. Cigarette Smoking, CFH, APOE, ELOVL4 and Risk of Neovascular Age-Related Macular Degeneration. *Archives of Ophthalmology* (2007) January; 125(1): 49-54) and as can be seen on the expanded population in FIG. 5, the presence of one C allele for CFH Y402H was not significantly associated with neovascular AMD risk ($P>0.2$). Together, the findings in this study validated that the 10q26 region was more strongly associated with neovascular AMD than the 1q32 region where CFH resides (Dewan, A. et al. HTRA1 promoter polymorphism in wet age-related macular degeneration. *Science* (2006) 314, 989-992; Yang, Z. et al. A variant of the HTRA1 gene increases susceptibility to age-related macular degeneration. *Science* (2006) 314, 992-993; Shuler, R. K., Jr. et al. Neovascular age-related macular degeneration and its association with LOC387715 and complement factor H polymorphism. *Arch. Ophthalmol.* (2007) 125, 63-67).

For each of the significant SNPs in the 10q26 region, there were no interactions between the homozygous or heterozygous genotypes and smoking, nor between the homozygous and heterozygous genotypes and CFH CC genotype.

The population attributable risk (PAR) for not having one protective minor allele at rs2672598 or being homozygous for CFH Y402H or smoking ≧10 pack-years was 75%. The combination of risk factors including having the risk allele for any of the SNPs rs10490924, rs11200638, rs1049331, or rs2293870, or being homozygous for CFH Y402H, or smoking ≧10 pack-years explained about 80% of the risk in the total population (FIGS. 6A and 6B).

The functional effect of the SNPs newly identified as significantly associated with AMD susceptibility was assessed. Given that SNP rs10664316 is located 4,782 bp upstream of the first HTRA1 coding ATG and is not well conserved (web site at www.ensembl.org/gene=ENSG00000166033), attention was focused on the SNPs identified in the promoter and exon 1 of the HTRA1 gene. From the computer program MapInspector (web site at www.genomatrix.de/), it appears that the protective allele for SNP rs2672598 creates a binding site for the transcription factor ELK-1. ELK-1 activity was reported to be impaired in a patient with a premature form of aging and insulin resistance (Knebel, B., Avci, H., Bullmann, C., Kotzka, J., & Muller-Wieland, D. Reduced phosphorylation of transcription factor Elk-1 in cultured fibroblasts of a patient with premature aging syndrome and insulin resistance. *Exp. Clin. Endocrinol. Diabetes* (2005) 113, 94-101). If the risk allele of the promoter SNP rs1200638 results in increased expression of HTRA1 (Dewan, A. et al. HTRA1 promoter polymorphism in wet age-related macular degeneration. *Science* (2006) 314, 989-992; Yang, Z. et al. A variant of the HTRA1 gene increases susceptibility to age-related macular degeneration. *Science* (2006) 314, 992-993), then it is contemplated that the minor allele of rs2672598 exerts a protective effect by enabling the binding of ELK-1, which could downregulate the expression of HTRA1. SNP rs2293870 is located in one of the HTRA1 binding domains for insulin like growth factors (IGFs) (web site at http://smart.embl-heidelberg.de/smart/do) (Clausen, T., Southan, C., & Ehrmann, M. The HtrA family of proteases: implications for protein composition and cell fate. *Mol. Cell* (2002) 10, 443-455). IGF has been implicated in other ocular conditions characterized by neovascularization such as diabetic retinopathy and retinopathy of prematurity (Chen, J. & Smith, L. E. Retinopathy of prematurity. *Angiogenesis.* (2007) 10, 133-140). Therefore, the effect of rs2293870 on a regulatory pathway involving HTRA1 and IGFs has biologic plausibility for AMD.

In summary, in a population of extremely discordant sibling pairs, variants in the HTRA1 region were newly identified that both increase and decrease risk of developing neovascular AMD. These findings validate the fact that HTRA1 is the likely candidate gene in the 10q26 region. Although other variants in the hypothetical LOC387715 locus were identified that may ultimately play a role in AMD susceptibility (Greally, J. M. Genomics: Encyclopaedia of humble DNA. *Nature* (2007) 447, 782-783; The ENCODE Project Consortium, Identification and analysis of functional elements in 1% of the human genome by the ENCODE pilot project. *Nature* (2007) 447, 799-816), the newly described variants in HTRA1 have contemplated functional regulatory effects, suggesting etiologic mechanisms. The study presented here demonstrated that HTRA1 variants influence risk independent of CFH genotype and smoking, supporting the role for HTRA1 in a distinct pathway underlying AMD pathogenesis.

Methods

Patient Population

The protocol was reviewed and approved by the Institutional Review Board at the Massachusetts Eye & Ear Infirmary (MEEI) and conforms to the tenets of the Declaration of Helsinki. Eligible patients were enrolled in this study after they gave informed consent either in person, over the phone, or through the mail, before answering questions to a standardized questionnaire and donating 10 to 50 ml of venous blood.

Index patients with neovascular AMD were recruited from the Retina Service of the MEEI and the Associated Retina Consultants at the Beaumont Hospital (Royal Oak, Mich.). Details of the recruitment and the clinical description of the patients are described elsewhere (DeAngelis, M. M. et al. Extremely discordant sib-pair study design to determine risk factors for neovascular age-related macular degeneration. *Arch. Ophthalmol.* (2004) 122, 575-580). In brief, all index patients had the neovascular form of AMD in at least one eye, defined by subretinal hemorrhage, fibrosis, or fluorescein angiographic presence of neovascularization documented at the time of, or prior to, enrollment in the study (AMD level "4b" on the AREDS scale). The unaffected siblings had normal maculae at an age older than that at which the index patient was first diagnosed with neovascular AMD. Normal maculae (defined as the zone centered at the foveola and extending 2 disc diameters, or 3000 microns, in radius) fulfilled the following criteria: 0-5 small drusen, (all less than 63 microns in diameter), no pigment abnormalities, no geographic atrophy, and no neovascularization (as defined previously (The Age-Related Eye Disease Study system for classifying age-related macular degeneration from stereoscopic color fundus photographs: the Age-Related Eye Disease Study Report Number 6. *Am. J. Ophthalmol.* (2001) 132, 668-681; Davis, M. D. et al. The Age-Related Eye Disease Study severity scale for age-related macular degeneration: AREDS Report No. 17. *Arch. Ophthalmol.* (2005) 123, 1484-1498)) (AMD levels "0" or "1" on the AREDS scale). Disease status of every participant was confirmed by at least two investigators by evaluation of fundus photographs or fluorescein angiograms except when one of the investigators directly examined an unaffected sibling during a home visit (n=6 cases).

Smoking Exposure

A standardized questionnaire was administered to all eligible participants in person or over the phone to ascertain smoking exposure, with the age of the index patient at the time of the fundus photographs as cutoff reference age for smoking exposure for all members in a sibship. In most cases the diagnosis of AMD was made simultaneously with the diagnosis of neovascular AMD. If a participant ever smoked, the age was recorded when they started smoking, the age when they quit smoking (if they did quit), and the number of packs of cigarettes smoked per day, on average. Based on the responses, the number of pack-years of cigarettes smoked was calculated for each smoker. Participants who smoked less than 100 cigarettes during their lifetime (i.e., less than $1/73$ of a pack-year) were categorized as having never smoked. A pack-year was defined as one pack of cigarettes per day for one year, with one pack defined as twenty cigarettes. For statistical analysis (see below), the reference cutoff for smoking was defined as greater than or equal to 10 pack-years versus less than 10 pack-years. With this cutoff, the subjects in this study were divided into two approximately equal groups (DeAngelis, M. M. et al. Cigarette Smoking, CFH, APOE, ELOVL4 and Risk of Neovascular Age-Related Macular Degeneration. *Archives of Ophthalmology* (2007) January; 125(1):49-54).

Genotyping Analysis

Leukocyte DNA was either purified by using standard phenol-chloroform or DNAzol (Invitrogen Corporation, Carlsbad, Calif.) extraction protocols. Previously reported oligonucleotide primers were used to amplify the coding region and flanking intronic sequences of exon 12 for PLEKHA1 (Rivera, A. et al. Hypothetical LOC387715 is a second major susceptibility gene for age-related macular degeneration, contributing independently of complement factor H to disease risk. *Hum. Mol. Genet.* (2005) 14, 3227-3236), exon 9 of CFH (Haines, J. L. et al. Complement factor H variant increases the risk of age-related macular degeneration. *Science* (2005) 308, 419-421) and the promoter sequence for HTRA1 (Dewan, A. et al. HTRA1 promoter polymorphism in wet age-related macular degeneration. *Science* (2006) 314, 989-992). For the putative LOC387715 gene region (including both exons) and the 9 exons of HTRA1, oligonucleotide primers were selected using the Primer3 program (primer3.sourceforge.net/) to encompass the entire coding region and flanking intronic sequences (FIG. 9).

For all four genes, the polymerase chain reaction was used to amplify genomic DNA fragments from 20 ng of leukocyte DNA in a solution of 10×PCR buffer containing 25 mM of $MgCl_2$, 0.2 mM each of dATP, dTTP, dGTP, and CTP, and 0.5 units of Taq DNA polymerase (USB Corporation, Cleveland, Ohio). For the PLEKHA1 and HTRA1 genes, 5 M Betaine was added to each PCR reaction (Sigma-Aldrich, St. Louis, Mo.). The temperatures used during the polymerase chain reaction were as follows: for PLEKHA1 and HTRA1, 95° C. for 5 minutes followed by 35 cycles of 60° C. for 30 seconds, 72° C. for 30 seconds and 95° C. for 30 seconds, with a final annealing at 60° C. for 1.5 minutes and extension of 72° C. for 5 minutes; for LOC387715, 95° C. for 5 minutes followed by 35 cycles of 62° C. for 30 seconds, 72° C. for 30 seconds and 95° C. for 30 seconds, with a final annealing at 62° C. for 1.5 minutes and extension of 72° C. for 5 minutes; for CFH, 95° C. for 5 minutes followed by 35 cycles of 56° C. for 30 seconds, 72° C. for 30 seconds and 95° C. for 30 seconds, with a final annealing at 56° C. for 1.5 minutes and extension of 72° C. for 5 minutes; for sequencing reactions, PCR products were digested according to manufacturer's protocol with ExoSAP-IT (USB Corporation, Cleveland, Ohio) then were subjected to a cycle sequencing reaction using the Big Dye Terminator v3.1 Cycle Sequencing kit (Applied Biosystems, Foster City, Calif.) according to manufacturer's protocol. Products were purified with Performa DTR Ultra 96-well plates (Edge Biosystems, Gaithersburg, Md.) in order to remove excess dye terminators. Samples were sequenced on an ABI Prism 3100 DNA sequencer (Applied Biosystems, Foster City, Calif.). Electropherograms generated from the ABI Prism 3100 were analyzed using the Lasergene DNA and protein analysis software (DNASTAR, Inc., Madison, Wis.). Electropherograms were read by two independent evaluators without knowledge of the subject's disease status. All patients were sequenced in the forward direction (5' to 3'), unless variants, polymorphisms, or mutations were identified, in which case confirmation was obtained in some cases by sequencing in the reverse direction.

Genotyping of Microsatellite Markers

Eight highly heterozygous microsatellite markers spanning 33 megabases of the 10q26 region were analyzed (FIG. 3 and FIG. 7), these markers included several that were tightly linked to PLEKHA1, LOC387715 and HTRA1 (FIG. 9). All markers were fluorescently labeled with either HEX or FAM on the 5' end of the reverse primer and an additional sequence of CTGTCTT was added to the 5' of the forward primer. The polymerase chain reaction was used to amplify genomic DNA fragments from 20 ng of leukocyte DNA in a solution of 10×PCR buffer containing 25 mM of $MgCl_2$, 0.2 mM each of dATP, dTTP, dGTP, and dCTP, and 0.5 units of Taq DNA polymerase (USB Corporation, Cleveland, Ohio). The temperatures used during the polymerase chain reaction were as follows: 95° C. for 5 minutes followed by 35 cycles of 54-60° C. (specific to primer pair) for 30 seconds, 72° C. for 30 seconds and 95° C. for 30 seconds, with a final annealing at 54-60° C. (specific to primer pair) for 1.5 minutes and extension of 72° C. for 5 minutes. PCR products were diluted 1:20 for markers labeled with FAM and 1:10 for markers labeled with HEX. Samples were pooled according to product size and denatured before being genotyped on the ABI 3730x1 DNA Analyzer(Applied Biosystems, Foster City, Calif.). Data was then analyzed using ABI's Genemapper v3.7 software for analysis, which interrogated the quality of the size standard and made the appropriate genotype calls based on size. For quality control purposes, all genotypes were then evaluated manually.

Statistical Analyses

The program FBAT (biosun1.harvard.edu/~fbat/fbat.htm) which tests for Family Based Association was used to evaluate the effect of each SNP individually on risk of AMD (FIG. 2) (Horvath, S. et al. Family-based tests for associating haplotypes with general phenotype data: application to asthma genetics. *Genet. Epidemiol.* (2004) 26, 61-69). SNPs were only included for analysis in FBAT if the minor allele frequency (MAF) in the unaffected, and separately in the affected, siblings was greater than 5% and the number of informative families was not less than 4 (FIG. 2). A Bonferroni correction was applied to the point-wise P values that were calculated for each allele of the fourteen SNPs that met these criteria.

Haploview (web site at www.broad.mit.edu/mpg/haploview/) was used to generate the linkage disequilibrium plot (FIG. 1) among the nineteen identified SNPs that had a MAF greater than 5% (Barrett, J. C., Fry, B., Maller, J., & Daly, M. J. Haploview: analysis and visualization of LD and haplotype maps. *Bioinformatics*. (2005) 21, 263-265). Linkage disequilibrium ($r^2$) between each of the nineteen SNPs is depicted in FIG. 1. The haplotype blocks were constructed by Haploview by using the method proposed by Gabriel (Gabriel, S. B. et al. The structure of haplotype blocks in the human genome. *Science* (2002) 296, 2225-2229). Individual haplotypes were inferred and tested for association with AMD using FBAT (Horvath, S. et al. Family-based tests for associating haplotypes with general phenotype data: application to asthma genetics. *Genet. Epidemiol.* (2004) 26, 61-69).

Conditional logistic regression (CLR) (SAS 9.1, www.sas.com) was performed to identify factors associated with wet AMD. Potential risk factors of interest, as defined above, were evaluated initially one at a time. A multiple conditional logistic regression model for each significant SNP in the 10q26 region was built using those factors from the single factor model which appeared to be associated with neovascular AMD with a p value less than or equal to 0.1. CFH Y402H CT genotype was kept in the models, although its p>0.1, to more precisely adjust the effect of CFH. For each significant SNP, the minor allele (in unaffected siblings) in both the homozygous and heterozygous states versus the common allele in the homozygous state was examined in the model (FIG. 5).

Genotype and allele frequencies for all SNPs identified as significant were calculated in the affected and separately in unaffected siblings (FIGS. 11A and 11B). Deviation from Hardy-Weinberg Equilibrium (HWE) was tested on each SNP using the chi square test. Population Attributable Risk was calculated for the significant SNPs that were identified from the FBAT and CLR analysis for the 134 matched discordant sibpair data, where the relative risk (RR) was approximated by the odds ratio (Armitage, P. & Berry, G. *Statistical methods in medical research*(Blackwell Scientific Publications,1987) and was the proportion of cases exposed to the factor for each significant SNP in the 10q26 region.

For linkage analysis of the eight microsatellite markers, identity-by-state (IBS) scores were calculated from the number of alleles shared between each pair, the index and the discordant sibling, for each of the eight markers. Using heterozygosities for each marker obtained from Map-O-Mat (compgen.rutgers.edu/mapomat/), the expected IBS (null hypothesis of no linkage) was calculated and then compared with the observed IBS values. A goodness of fit test was applied to assess the significance of the difference between the observed and expected distribution. Bonferonni Correction was applied to the p values of the association tests on microsatellite markers and AMD risk.

Example 2

Use of Selective HTRA1 Antagonists

It is contemplated that a variety of selective HTRA1 antagonists, including but not limited to (1) a substance that selectively binds to HTRA1 and reduces the activity of HTRA1, and (2) a substance that reduces the HTRA1 gene expression, will be useful to slow down, stop, or reverse the progression of age-related macular degeneration. Examples of these compounds are listed herein.

For example, it is contemplated that an anti-HTRA1 antibody that binds to and reduces the activity of HTRA1 can be administered to an animal using techniques known to those skilled in the art so as to slow down, stop, or reverse the progression of age-related macular degeneration.

INCORPORATION BY REFERENCE

The entire content of each patent and non-patent document disclosed herein is expressly incorporated herein by reference for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A method of determining a human subject's risk of developing neovascular age-related macular degeneration, the method comprising detecting the presence of thymine or cytosine at a polymorphic site rs1049331 of the HTRA1 gene from a sample obtained from the subject, wherein the presence of thymine for one or both alleles indicates the subject is more likely to develop neovascular age-related macular degeneration than a subject homozygous for cytosine.

2. The method of claim 1, wherein the subject heterozygous for thymine is 6-fold more likely to develop neovascular age-related macular degeneration than a subject homozygous for cytosine.

3. The method of claim 1, wherein the subject homozygous for thymine is 106-fold more likely to develop neovascular age-related macular degeneration than a subject homozygous for cytosine.

4. The method of claim 1, wherein the thymine or cytosine is detected by direct nucleotide sequencing.

5. The method of claim 1, wherein the thymine or cytosine is detected by hybridization using a hybridization probe that selectively anneals to the thymine or cytosine at the polymorphic site of the HTRA1 gene.

6. The method of any one of claims 4 and 5, further comprising the step of amplifying the polymorphic site prior to detecting the presence of thymine or cytosine.

7. The method of claim 1, wherein the thymine or cytosine is detected by an amplification reaction using primers capable of amplifying the polymorphic site.

8. The method of claim 1, wherein the method further comprises detecting whether the subject has a polymorphism at a second polymorphic site of the HTRA1 gene.

9. The method of claim 8, wherein the second polymorphic site is Rs2293870.

10. The method of claim 1, wherein the detecting step comprises examination of mRNA transcribed from HTRA1.

11. The method of claim 1, wherein the thymine or cytosine is detected by an assay selected from the group consisting of a restriction fragment length polymorphism assay, denaturing gradient gel electrophoresis, single-strand confirmation polymorphism analysis, denaturing high performance liquid chromatography, and a molecular beacon assay.

\* \* \* \* \*

UNITED STATES PATENT AND TRADEMARK OFFICE
CERTIFICATE OF CORRECTION

| | | |
|---|---|---|
| PATENT NO. | : 7,972,787 B2 | Page 1 of 1 |
| APPLICATION NO. | : 12/032154 | |
| DATED | : July 5, 2011 | |
| INVENTOR(S) | : DeAngelis | |

It is certified that error appears in the above-identified patent and that said Letters Patent is hereby corrected as shown below:

Title page 1, Item (12) and (75) in the section entitled "Inventor," replace "Margaret M. Deangelis" with --Margaret M. DeAngelis--.

In column 1, lines 14-17, remove the paragraph under the heading GOVERNMENT FUNDING and replace it with --The work described in this application was sponsored, in part, by the National Eye Institute under Grant No. EY-014458. The United States Government has certain rights in the invention.--.

In claim 9, column 40, line 21, replace "Rs2293870" with --rs2293870--.

Signed and Sealed this
Fourth Day of October, 2011

David J. Kappos
*Director of the United States Patent and Trademark Office*